US006787638B1

(12) United States Patent
Watkins et al.

(10) Patent No.: US 6,787,638 B1
(45) Date of Patent: Sep. 7, 2004

(54) TUMOR SPECIFIC HUMAN MONOCLONAL ANTIBODIES AND METHODS OF USE

(75) Inventors: Jeffry D. Watkins, Encinitas, CA (US); William D. Huse, Del Mar, CA (US)

(73) Assignee: Applied Molecular Evolution, Inc., San Diego, CA (US)

( * ) Notice: Subject to any disclaimer, the term of this patent is extended or adjusted under 35 U.S.C. 154(b) by 0 days.

(21) Appl. No.: 09/203,768

(22) Filed: Dec. 2, 1998

(51) Int. Cl.$^7$ .............................................. C07K 16/00
(52) U.S. Cl. ........................... 530/388.85; 530/388.15; 530/391.7; 424/142.1
(58) Field of Search .......................... 530/387.1, 387.3, 530/388.1, 388.8, 388.85, 391.3, 391.7; 424/130.1, 133.1, 156.1, 183.1, 178.1

(56) References Cited

U.S. PATENT DOCUMENTS 5,106,738 A    4/1992   Hanna, Jr. et al.

FOREIGN PATENT DOCUMENTS

| CA | 2 162 577 A | 11/1994 |
|---|---|---|
| FR | 2 751 346 A | 1/1998 |
| WO | WO 91/09135 | 6/1991 |
| WO | WO 91/0996 | * 7/1991 |
| WO | WO 94/26895 | 11/1994 |

OTHER PUBLICATIONS

Colman (Research in Immunology 145:33–36, 1994).*
Freshney (Culture of Animal Cells, A Manual of Basic Technique, Alan R. Liss, Inc., 1983, New York, p4).*
Dermer (Bio/Technology, 1994, 12:320).*
Gura (Science, 1997, 278:1041–1042).*
Jain (Sci. Am., 1994, 271:58–65).*
Amit et al., Science 233:747–753, 1986.*
Panka et al., Proc. Natl. Acad. Sci. USA 85:3080–3084, 1988.*
Rudikoff et al., Proc. Natl. Acad. Sci. USA 79:1979–82, 1982.*
Boerner et al., "Production of Antigen–Specific Human Monoclonal Antibodies From In Vitro–Primed Human Splenocytes", *The Journal of Immunology*, 147 (1):86–95 (1991).
Bohn et al., Human Monoclonal IgM Antibodies from Foetal B–Cell Hybriodomas Directed Against a Surface Antigen on Human Tumour Cells, *Res. Immunol.*, 143:879–891 (1992).
Carroll et al., "Mouse X Human Heterohybridomas as Fusion Partners with Human B Cell Tumors", *Journal of Immunological Methods*, 89:61–72 (1986).
Cole et al, "A Strategy for the Production of Human Monoclonal Antibodies Reactive with Lung Tumor Cell Lines", *Cancer Research*, 44:2750–2753 (1984).
Cote et al., "Generation of Human Monoclonal Antibodies Reactive with Cellular Antigens", *Proc. Natl. Acad. Sci. USA*, 80:2026–2030 (1983).

Cote et al., "Specificity Analysis of Human Monoclonal Antibodies Reactive with Cell Surface and Intracellular Antigens", *Proc. Natl. Acad. Sci. USA*, 83:2959–2963 (1986).
Glassy, Mark C., "Immortalization of Human Lymphocytes from a Tumor–Involved Lymph Node", *Cancer Research*, 47:5181–5188 (1987).
Haspel, et al., "Generation of Tumor Cell–Reactive Human Monoclonal Antibodies Using Peripheral Blood Lymphocytes from Actively Immunized Colorectal Carcinoma Patients", *Cancer Research*, 45:3951–3961 (1985).
Irie et al., "Human Antibody to OFA–I, a Tumor Antigen, Produced in vitro by Epstein–Barr Virus–Transformed Human B–Lymphoid Cell Lines", *Proc. Natl. Acad. Sci. USA*, 79:5666–5670 (1982).
Kan–Mitchell et al., "Human Monoclonal Antibodies Directed Against Melanoma Tumor–Associated Antigen", *Cancer Research*, 46:2490–2496 (1986).
Koda et al, "Generation of Human Monoclonal Antibodies Against colon Cancer", *Arch. Surgery*, 125:1591–1597 (1990).
Kozbor et al., "Human Hybridomas Constructed with Antigen–Specific Epstein–Barr Virus–Transformed Cell Lines", *Proc. Natl. Acad. Sci. USA*, 79:6651–6655 (1982).
Kozbor and Roder, "In vitro Stimulated Lymphocytes as a Source of Human Hybridomas", *Eur. J. Immunol.*, 14:23–27 (1984).
Liu et al., "Production of Anti–Tumor Human Monoclonal Antibodies Using Different Approaches", *Hum. Antibod. Hybridomas*, 4:2–8 (1993).
Schlom et al., "Generation of Human Monoclonal Antibodies Reactive with Human Mammary Carcinoma Cells", *Proc. Natl. Acad. Sci. USA*, 77:6841–6845 (1980).
Sikora and Wright, "Human Monoclonal Antibodies to Lung–Cancer Antigens", *Br. J. Cancer*, 43:696–700 (1981).
Zhang et al., "A Human Monoclonal Antimelanoma Single–Chain Fv Antibody Derived from Tumor–Infiltrating Lymphocytes", *Cancer Research*, 55:3584–3591 (1995).

(List continued on next page.)

*Primary Examiner*—Larry R. Helms
(74) *Attorney, Agent, or Firm*—McDermott Will & Emery LLP

(57) ABSTRACT

The invention provides tumor-specific human monoclonal antibodies and functional fragments. Also provided are nucleic acids encoding tumor-specific human monoclonal antibodies and functional fragments. A method for reducing neoplastic cell proliferation is also provided. The method consists of administering an effective amount of a tumor-specific human monoclonal antibody or functional fragment. Also provided is a method of detecting a neoplastic cell in a sample. The method consists of contacting a cell with a tumor-specific monoclonal antibody or functional fragment and detecting the specific binding of the human monoclonal antibody or functional fragment to the sample.

7 Claims, 4 Drawing Sheets

OTHER PUBLICATIONS

Eulitz et al., "Distinctive Serologic, Chemical, and Molecular Properties of Human λIV Light Chains," *J. Immun.* 157(7):3256–3265 (1995).

Hamblin et al., "Unmutated Ig $V_h$ Genes Are Associated with a More Aggressive Form of Chronic Lymphocytic Leukemia," *Blood* 94 (6):1848–1854 (1999).

Irie et al., "Human antibody to OFA–I, a tumor antigen, produced in vitro by epstein–barr virus–transformed human B–lymphoid cell lines," *Proc. Natl. Acad. Sci. U.S.A.* 79:5666–5670 (1982).

Reisner and Dagan, "The trimera mouse: generating human monoclonal antibodies and an animal model for human diseases," *Tibtech* 16:242–246 (1998).

\* cited by examiner

SEQUENCE LISTING

```
<160> NUMBER OF SEQ ID NOS:  8

<210> SEQ ID NO 1
<211> LENGTH: 417
<212> TYPE: DNA
<213> ORGANISM: Homo sapiens
<220> FEATURE:
<221> NAME/KEY: CDS
<222> LOCATION: (1)..(417)
<221> NAME/KEY: sig_peptide
<222> LOCATION: (1)..(57)

<400> SEQUENCE: 1 atg aaa cac ctg tgg ttc ttc ctc ctc ctg gtg gca gct ccc aga tgg      48
Met Lys His Leu Trp Phe Phe Leu Leu Leu Val Ala Ala Pro Arg Trp
  1               5                  10                  15 gtc ctg tcc cag gtg cag cta cag cag tgg ggc gca gga ctg ttg aag      96
Val Leu Ser Gln Val Gln Leu Gln Gln Trp Gly Ala Gly Leu Leu Lys
             20                  25                  30 cct tcg gag acc ctg tcc ctc acc tgc gct gtc tat ggt ggg tcc ttc     144
```

```
                Pro Ser Glu Thr Leu Ser Leu Thr Cys Ala Val Tyr Gly Gly Ser Phe
                         35                  40                  45 agt ggt tac tac tgg agc tgg atc cgc cag ccc cca ggg aag ggg ctg            192
Ser Gly Tyr Tyr Trp Ser Trp Ile Arg Gln Pro Pro Gly Lys Gly Leu
         50                  55                  60 gag tgg att ggg gaa atc aat cat agt gga agc acc aac tac aac ccg            240
Glu Trp Ile Gly Glu Ile Asn His Ser Gly Ser Thr Asn Tyr Asn Pro
 65                  70                  75                  80 tcc ctc aag agt cga gtc acc ata tca gta gac acg tcc aag aac cag            288
Ser Leu Lys Ser Arg Val Thr Ile Ser Val Asp Thr Ser Lys Asn Gln
                 85                  90                  95 ttc tcc ctg aag ctg agc tct gtg acc gcc gcg gac acg gct gtg tat            336
Phe Ser Leu Lys Leu Ser Ser Val Thr Ala Ala Asp Thr Ala Val Tyr
                100                 105                 110 tac tgt gcg aga gaa ata gca gct cgt cct cac cga tac ttt gac tac            384
Tyr Cys Ala Arg Glu Ile Ala Ala Arg Pro His Arg Tyr Phe Asp Tyr
            115                 120                 125 tgg ggc cag gga acc ctg gtc acc gtc tcc tca                                417
Trp Gly Gln Gly Thr Leu Val Thr Val Ser Ser
        130                 135
```

<210> SEQ ID NO 2
<211> LENGTH: 139
<212> TYPE: PRT
<213> ORGANISM: Homo sapiens

<400> SEQUENCE: 2

```
Met Lys His Leu Trp Phe Phe Leu Leu Leu Val Ala Ala Pro Arg Trp
 1               5                  10                  15

Val Leu Ser Gln Val Gln Leu Gln Gln Trp Gly Ala Gly Leu Leu Lys
             20                  25                  30

Pro Ser Glu Thr Leu Ser Leu Thr Cys Ala Val Tyr Gly Gly Ser Phe
         35                  40                  45

Ser Gly Tyr Tyr Trp Ser Trp Ile Arg Gln Pro Pro Gly Lys Gly Leu
     50                  55                  60

Glu Trp Ile Gly Glu Ile Asn His Ser Gly Ser Thr Asn Tyr Asn Pro
 65                  70                  75                  80

Ser Leu Lys Ser Arg Val Thr Ile Ser Val Asp Thr Ser Lys Asn Gln
                 85                  90                  95

Phe Ser Leu Lys Leu Ser Ser Val Thr Ala Ala Asp Thr Ala Val Tyr
                100                 105                 110

Tyr Cys Ala Arg Glu Ile Ala Ala Arg Pro His Arg Tyr Phe Asp Tyr
            115                 120                 125

Trp Gly Gln Gly Thr Leu Val Thr Val Ser Ser
        130                 135
```

<210> SEQ ID NO 3
<211> LENGTH: 351
<212> TYPE: DNA
<213> ORGANISM: Homo sapiens
<220> FEATURE:
<221> NAME/KEY: CDS
<222> LOCATION: (1)..(351)
<221> NAME/KEY: sig_peptide
<222> LOCATION: (1)..(24)

<400> SEQUENCE: 3

```
ctc tgg ctc cca gat acc act gga gaa ata gtg atg acg cag tct cca             48
Leu Trp Leu Pro Asp Thr Thr Gly Glu Ile Val Met Thr Gln Ser Pro
 1               5                  10                  15
```

```
gcc acc ctg tct gtg tct cca ggg gaa aga gcc acc ctc tcc tgc agg    96
Ala Thr Leu Ser Val Ser Pro Gly Glu Arg Ala Thr Leu Ser Cys Arg
             20                  25                  30 gcc agt cag agt gtt agc agc aac tta gcc tgg tac cag cag aaa cct   144
Ala Ser Gln Ser Val Ser Ser Asn Leu Ala Trp Tyr Gln Gln Lys Pro
         35                  40                  45 ggc cag gct ccc agg ctc ctc atc tat ggt gca tcc acc agg gcc act   192
Gly Gln Ala Pro Arg Leu Leu Ile Tyr Gly Ala Ser Thr Arg Ala Thr
 50                  55                  60 ggt atc cca gcc agg ttc agt ggc agt ggg tct ggg aca gag ttc act   240
Gly Ile Pro Ala Arg Phe Ser Gly Ser Gly Ser Gly Thr Glu Phe Thr
 65                  70                  75                  80 ctc acc atc agc agc ctg cag tct gaa gat ttt gca gtt tat tac tgt   288
Leu Thr Ile Ser Ser Leu Gln Ser Glu Asp Phe Ala Val Tyr Tyr Cys
                 85                  90                  95 cag cag tat aat aac tgg cct ccg tac act ttt ggc cag ggg acc aag   336
Gln Gln Tyr Asn Asn Trp Pro Pro Tyr Thr Phe Gly Gln Gly Thr Lys
             100                 105                 110 ctg gag atc aaa cga                                               351
Leu Glu Ile Lys Arg
        115

<210> SEQ ID NO 4
<211> LENGTH: 117
<212> TYPE: PRT
<213> ORGANISM: Homo sapiens

<400> SEQUENCE: 4

Leu Trp Leu Pro Asp Thr Thr Gly Glu Ile Val Met Thr Gln Ser Pro
 1               5                   10                  15

Ala Thr Leu Ser Val Ser Pro Gly Glu Arg Ala Thr Leu Ser Cys Arg
             20                  25                  30

Ala Ser Gln Ser Val Ser Ser Asn Leu Ala Trp Tyr Gln Gln Lys Pro
         35                  40                  45

Gly Gln Ala Pro Arg Leu Leu Ile Tyr Gly Ala Ser Thr Arg Ala Thr
 50                  55                  60

Gly Ile Pro Ala Arg Phe Ser Gly Ser Gly Ser Gly Thr Glu Phe Thr
 65                  70                  75                  80

Leu Thr Ile Ser Ser Leu Gln Ser Glu Asp Phe Ala Val Tyr Tyr Cys
                 85                  90                  95

Gln Gln Tyr Asn Asn Trp Pro Pro Tyr Thr Phe Gly Gln Gly Thr Lys
             100                 105                 110

Leu Glu Ile Lys Arg
        115

<210> SEQ ID NO 5
<211> LENGTH: 354
<212> TYPE: DNA
<213> ORGANISM: Homo sapiens
<220> FEATURE:
<221> NAME/KEY: CDS
<222> LOCATION: (1)..(354)

<400> SEQUENCE: 5 cag gtg cag ctg gtg cag tct ggg gct gag gtg aag aag cct ggg tcc    48
Gln Val Gln Leu Val Gln Ser Gly Ala Glu Val Lys Lys Pro Gly Ser
 1               5                   10                  15 tcg gtg aag gtc tcc tgc aag gct tct gga ggc acc ttc agc agc tat    96
Ser Val Lys Val Ser Cys Lys Ala Ser Gly Gly Thr Phe Ser Ser Tyr
             20                  25                  30
```

```
gct atc agc tgg gtg cga cag gcc cct gga caa ggg ctt gag tgg atg      144
Ala Ile Ser Trp Val Arg Gln Ala Pro Gly Gln Gly Leu Glu Trp Met
        35                  40                  45 gga ggg atc atc cct atc ttt ggt aca gca aac tac gca cag aag ttc      192
Gly Gly Ile Ile Pro Ile Phe Gly Thr Ala Asn Tyr Ala Gln Lys Phe
 50                  55                  60 cag ggc aga gtc acg att acc gcg gac gaa tcc acg agc aca gcc tac      240
Gln Gly Arg Val Thr Ile Thr Ala Asp Glu Ser Thr Ser Thr Ala Tyr
 65                  70                  75                  80 atg gag ctg agc agc ctg aga tct gag gac acg gcc gtg tat tac tgt      288
Met Glu Leu Ser Ser Leu Arg Ser Glu Asp Thr Ala Val Tyr Tyr Cys
                 85                  90                  95 gcg aga gaa gat agc agt ggc tgg tat cac tac tgg ggc cag gga acc      336
Ala Arg Glu Asp Ser Ser Gly Trp Tyr His Tyr Trp Gly Gln Gly Thr
            100                 105                 110 ctg gtc acc gtc tcc tca                                               354
Leu Val Thr Val Ser Ser
        115

<210> SEQ ID NO 6
<211> LENGTH: 118
<212> TYPE: PRT
<213> ORGANISM: Homo sapiens

<400> SEQUENCE: 6

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Asp Ser Ser Gly Trp Tyr His Tyr Trp Gly Gln Gly Thr
            100                 105                 110

Leu Val Thr Val Ser Ser
        115

<210> SEQ ID NO 7
<211> LENGTH: 333
<212> TYPE: DNA
<213> ORGANISM: Homo sapiens
<220> FEATURE:
<221> NAME/KEY: CDS
<222> LOCATION: (1)..(333)

<400> SEQUENCE: 7 tct tct gag ctg act cag gac cct gct gtg tct gtg gcc ttg gga cag       48
Ser Ser Glu Leu Thr Gln Asp Pro Ala Val Ser Val Ala Leu Gly Gln
  1               5                  10                  15 aca gtc agg atc aca tgc caa gga gac agc ctc aga agc tat tat gca       96
Thr Val Arg Ile Thr Cys Gln Gly Asp Ser Leu Arg Ser Tyr Tyr Ala
             20                  25                  30 agc tgg tac cag cag aag cca gga cag gcc cct gta ctt gtc atc tat      144
Ser Trp Tyr Gln Gln Lys Pro Gly Gln Ala Pro Val Leu Val Ile Tyr
        35                  40                  45
```

-continued

```
ggt aaa aac aac cgg ccc tca ggg atc cca gac cga ttc tct ggc tcc        192
Gly Lys Asn Asn Arg Pro Ser Gly Ile Pro Asp Arg Phe Ser Gly Ser
     50                  55                  60 agc tca gga aac aca gct tcc ttg acc atc act ggg gct cag gcg gaa        240
Ser Ser Gly Asn Thr Ala Ser Leu Thr Ile Thr Gly Ala Gln Ala Glu
 65                  70                  75                  80 gat gag gct gac tat tac tgt aac tcc cgg gac agc agt ggt aac ccc        288
Asp Glu Ala Asp Tyr Tyr Cys Asn Ser Arg Asp Ser Ser Gly Asn Pro
                 85                  90                  95 gtg gta ttc ggc gga ggg acc aag ctg acc gtc cta ggt cag ccc            333
Val Val Phe Gly Gly Gly Thr Lys Leu Thr Val Leu Gly Gln Pro
             100                 105                 110

<210> SEQ ID NO 8
<211> LENGTH: 111
<212> TYPE: PRT
<213> ORGANISM: Homo sapiens

<400> SEQUENCE: 8

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn Pro
                 85                  90                  95

Val Val Phe Gly Gly Gly Thr Lys Leu Thr Val Leu Gly Gln Pro
             100                 105                 110
```

US 6,787,638 B1

TUMOR SPECIFIC HUMAN MONOCLONAL ANTIBODIES AND METHODS OF USE

BACKGROUND OF THE INVENTION

The present invention relates generally to cancer and, more specifically, to human monoclonal antibodies for the treatment and diagnosis of cancer.

Cancer is one of the leading causes of death in the United States. Each year, more than half a million Americans die from cancer, and more than one million are newly diagnosed with the disease. In cancer, neoplastic cells escape from their normal growth regulatory mechanisms and proliferate in an uncontrolled fashion, leading to the development of a malignant tumor. Tumor cells can metastasize to secondary sites if treatment of the primary tumor is either not complete or not initiated before substantial progression of the disease. Early diagnosis and effective treatment of malignant tumors is therefore essential for survival.

The current methods for treating cancer include surgery, radiation therapy and chemotherapy. A major problem with each of these treatments is their lack of specificity for cancer cells. For instance, surgical removal of the tumor is often incomplete. Even a few residual neoplastic cells can be lethal, as they can rapidly proliferate and metastasize to other sites. Radiation and chemotherapy also have serious limitations. These therapies target all growing cells of the body, including both normal and neoplastic cells. Due to their toxicity to normal tissues, the amount of radiation or chemotherapeutic agent that can be safely used is often inadequate to kill all neoplastic cells. Additionally, their toxicity to normal tissues is manifested by unpleasant side effects, including nausea and hair loss, that severely reduce the quality of life for the cancer patient undergoing these treatments. Clearly, a more selective and effective means of treating cancer is needed.

Monoclonal antibodies are homogeneous preparations of immunoglobulin proteins that specifically recognize and bind to regions, or epitopes, of their corresponding antigens. Neoplastic cells selectively express antigens which are not present on normal cells. Thus, monoclonal antibodies can be produced that are directed against tumor-specific antigens. Such tumor-specific antigens can be linked to therapeutic moieties that kill or arrest the growth of neoplastic cells. In addition, monoclonal antibodies can be linked to diagnostic moieties that allow the imaging of neoplastic cells. Thus, monoclonal antibodies directed against antigens selectively expressed by tumor cells compared to normal cells can be beneficially used for the early detection and effective treatment of cancer.

Most current immunotherapeutic strategies for cancer have been of limited utility due to their reliance on mouse monoclonal antibodies. Mouse monoclonal antibodies can be produced easily and in virtually unlimited quantities using hybridoma technology. However, when administered to humans, they can be recognized as foreign by the human immune system and be neutralized before exerting their therapeutic effect on the diseased tissue. Furthermore, the murine immune system often preferentially recognizes immunodominant epitopes of normal human antigens present on tumor cells. Thus, human tumor-specific antigens often fail to generate therapeutically beneficial murine antibodies.

Human monoclonal antibodies can overcome both of these limitations. Most importantly, human monoclonal antibodies are not as immunogenic as murine antibodies. Therefore, tumor-specific human monoclonal antibodies will be able to more effectively target and eliminate neoplastic cells. Furthermore, the human immune system is less likely to generate antigens against epitopes present on normal cells, increasing the odds of generating and successfully identifying tumor-specific antigens. Additionally, the repertoire of the human immune system is different from that of the mouse, containing potentially novel antibody specificities.

Current procedures to produce tumor-specific human monoclonal antibodies have generally started with lymphocytes obtained from tumor-bearing patients. These procedures rely on the stimulation and expansion of tumor-reactive lymphoctyes in vivo. These procedures are seriously limited by the narrow range of antigen specificities of activated B-cells of cancer patients. As it is clearly not possible to immunize individuals in vivo with tumor cells, as one can with mice, it has not been possible to readily generate tumor-specific human monoclonal antibodies to any given antigen or tumor cell type. Procedures for generating tumor-specific antibodies of any desired specificity would be very beneficial for effective immunotherapy and immunodiagnosis.

Thus, there exists a need for improved tumor-specific human monoclonal antibodies for the therapy and diagnosis of cancer. The present invention satisfies this need and provides related advantages as well.

SUMMARY OF THE INVENTION

The invention provides a human monoclonal antibody or functional fragments thereof, having at least one Complementarity Determining Region (CDR) with substantially the amino acid sequence of a CDR of SEQ ID NO:2 or SEQ ID NO:4. Also provided is a human monoclonal antibody or functional fragment thereof, with at least one CDR having substantially the amino acid sequence of a CDR of SEQ ID NO:6 or SEQ ID NO:8. The invention also provides human monoclonal antibodies or functional fragments produced by the cell lines H1140, H2420 or H935. H1140, H2420 and H935 hybridoma cell lines are also provided.

The invention further provides a nucleic acid encoding a human monoclonal antibody or functional fragment thereof, having a nucleotide sequence encoding substantially the amino acid sequence of at least one CDR encoded by SEQ ID NO:1 or SEQ ID NO:3. Also provided is a nucleic acid encoding a human monoclonal antibody or functional fragment thereof, having a nucleotide sequence encoding substantially the amino acid sequence of at least one CDR encoded by SEQ ID NO:5 or SEQ ID NO:7.

A method for reducing neoplastic cell proliferation is also provided. The method consists of administering an effective amount of a human monoclonal antibody or functional fragment of the invention. Also provided is a method of detecting a neoplastic cell in a sample. The method consists of contacting a cell with a monoclonal antibody or functional fragment of the invention and detecting the specific binding of the human monoclonal antibody or functional fragment to the sample. The presence or increased level compared to a normal cell of the monoclonal antibody or functional fragment indicates the presence of a neoplastic cell in the sample.

BRIEF DESCRIPTION OF THE DRAWINGS

FIG. 1A shows fluorescent activated cell sorting (FACS) analysis using LH11238 antibody. FIG. 1B shows FACS analysis using LH13 antibody.

FIG. 2A shows that conditioned medium from H3396 cells (closed circles) competes for binding of LH13 antibody to fixed cell monolayers. FIG. 2B shows that LH13 antigen is secreted by H3396 cells and binds to culture dishes.

DETAILED DESCRIPTION OF THE INVENTION

Figure 1:
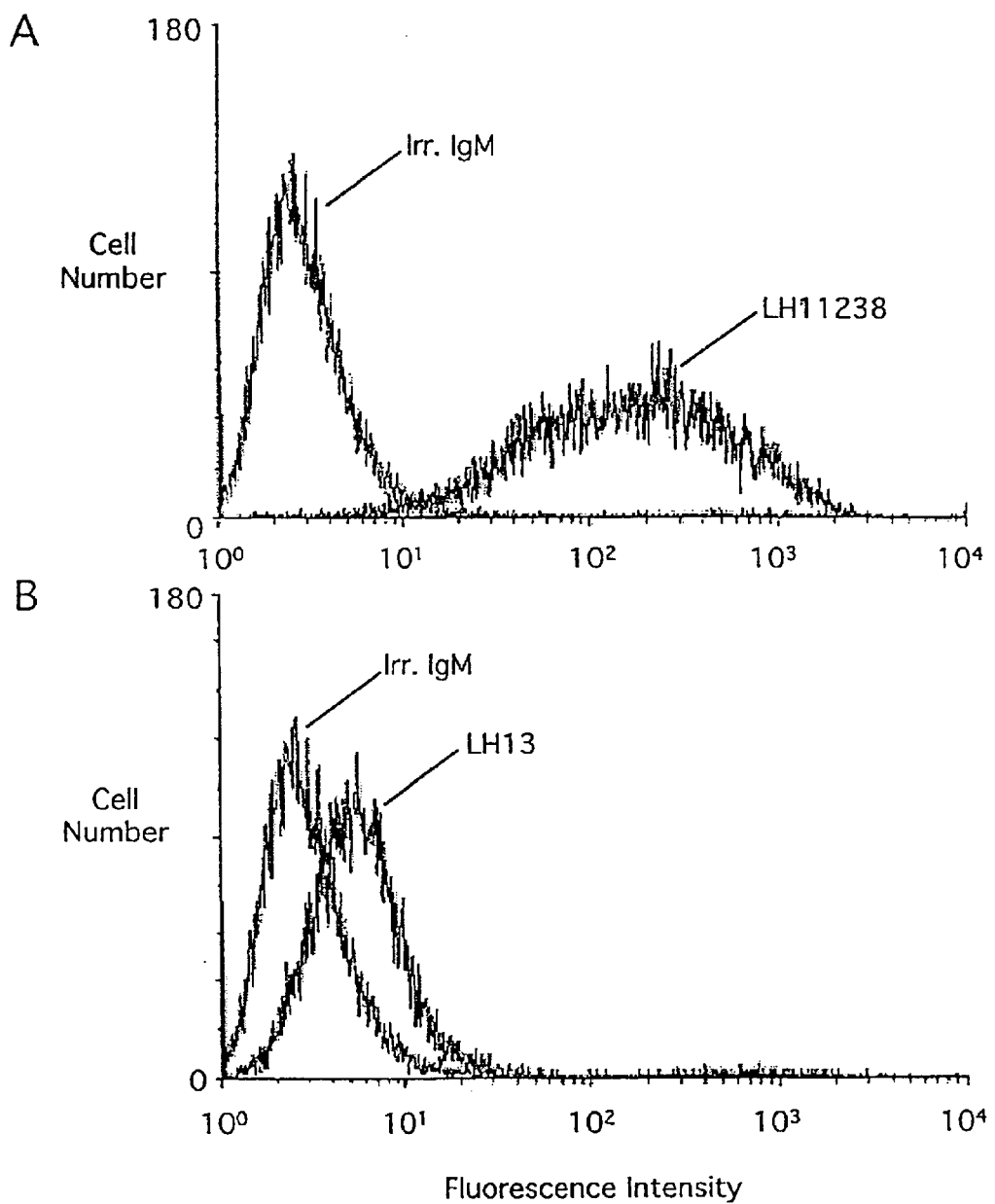
FIG. 1 shows the binding of LH11238 and LH13 antibodies to the surface of live H3464 cells.

The invention is directed to tumor-specific human monoclonal antibodies. The human monoclonal antibodies of the invention specifically bind to neoplastic cells compared to normal cells, and can be used for selectively targeting tumors. These antibodies are human in origin, and are unlikely to generate an immune response upon administration to a human subject. Therefore, these antibodies can be conjugated to cytotoxic or cytostatic agents and used to selectively target cancer cells for the elimination of tumors. The tumor-specific human monoclonal antibodies can also be used in diagnostic procedures to identify neoplastic cells. Early detection of cancer greatly increases the chances of an individual surviving the disease.

In one embodiment, the invention provides methods for generating hybridomas producing tumor-specific human monoclonal antibodies. Normal human splenocytes are immunized in vitro with tumor cells or tumor cell membranes in a mixed lymphocyte reaction. Such immunized splenocytes are then immortalized to produce hybridomas providing an unlimited supply of tumor-specific human monoclonal antibodies. Using normal cells as the source of lymphocytes greatly enlarges the repertoire of different tumor-specific antibodies that can be obtained for the treatment of cancer. Additionally, the type of cell or cell membrane used as the antigen in the method of the invention can be varied as needed to efficiently produce antibodies for different human therapeutic and diagnostic applications.

In another embodiment, the invention is directed to nucleic acids encoding human tumor-specific monoclonal antibodies. The nucleic acids can be used to express the encoded human antibodies or fragments thereof. Additionally, the encoding nucleic acids can be recombinantly engineered to produce modified human antibodies which exhibit higher affinity or higher selectivity for tumor cells or to augment other functional characteristics of the encoded antibodies. Such modified antibodies can additionally be constructed to contain other therapeutically advantageous modifications, such as enhanced association with cytotoxic agents or increased stimulation of the immune system.

In a further embodiment, the invention is directed to antigens recognized by the tumor-specific human monoclonal antibodies. The antigens can be used for cancer diagnostic procedures and to develop specific cytotoxic reagents for cancer therapy. Tumor-specific antigens can also be used as a vaccine and administered to individuals at risk of cancer to develop an effective immune response against neoplastic cells. The nucleic acids encoding the tumor-specific antigens can be used as probes in diagnostic procedures, or modified by recombinant methods to develop specific inhibitors of the antigen.

The basic structure of an immunoglobulin or antibody molecule consists of two identical light chains and two identical heavy chains, which associate non-covalently and can also be linked by disulfide bonds. Each heavy and light chain contains an amino-terminal variable region of about 110 amino acids and constant sequences in the remainder of the chain. The variable region includes several hypervariable regions, or complementarity-determining regions (CDRs) that form the antigen-binding site of the antibody molecule and determine its specificity. On either side of the CDRs of the heavy and light chains is the framework region, a relatively conserved sequence of amino acids that anchors and orients the CDRs. The constant region consists of one of five heavy chain sequences ($\mu$, $\gamma$, $\delta$, $\alpha$, or $\epsilon$) and one of two light chain sequences ($\kappa$ or $\lambda$). The heavy chain constant region sequences determine the isotype of the antibody and the effector functions of the molecule.

As used herein, the term "human monoclonal antibody" is intended to mean a monoclonal antibody comprising substantially the same heavy and light chain CDR amino acid sequences as found in a particular human immunoglobulin. An amino acid sequence which is substantially the same as a heavy or light chain CDR exhibits a considerable amount or extent of sequence identity when compared to a reference sequence. Such identity is definitively known or recognizable as representing the amino acid sequence of the particular human monoclonal antibody. Substantially the same heavy and light chain CDR amino acid sequence can have, for example, minor modifications or conservative substitutions of amino acids. Such a human monoclonal antibody maintains its function of selectively binding a tumor-specific antigen. The term "human monoclonal antibody" is intended to include a monoclonal antibody with substantially human CDR amino acid sequences produced, for example, by recombinant methods, by lymphocytes or by hybridoma cells.

As used herein, the term "CDR" is intended to mean the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901–917 (1987) and additionally by MacCallum et al., *J. Mol. Biol.* 262:732–745 (1996), which are incorporated herein by reference, where the definitions include overlapping or subsets of amino acid residues when compared against each other. Nevertheless, application of either definition to refer to a CDR of an antibody or functional fragment thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE I

CDR Definitions

|  | Kabat[1] | Chothia[2] | MacCallum[3] |
|---|---|---|---|
| $V_H$ CDR1 | 31–35 | 26–32 | 30–35 |
| $V_H$ CDR2 | 50–65 | 52–56 | 47–58 |
| $V_H$ CDR3 | 95–102 | 95–102 | 93–101 |
| $V_L$ CDR1 | 24–34 | 24–34 | 30–36 |

TABLE I-continued

CDR Definitions

|  | Kabat[1] | Chothia[2] | MacCallum[3] |
|---|---|---|---|
| $V_L$ CDR2 | 50–56 | 50–56 | 46–55 |
| $V_L$ CDR3 | 89–97 | 89–97 | 89–96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "functional fragment", when used in reference to a human monoclonal antibody, is intended to refer to a portion of the monoclonal antibody which still retains a functional activity. A functional activity can be, for example, antigen binding activity or specificity. A functional activity can also be, for example, an effector function provided by an antibody constant region. Human monoclonal antibody functional fragments include, for example, individual heavy or light chains and fragments thereof, such as VL, VH and Fd; monovalent fragments, such as Fv, Fab, and Fab'; bivalent fragments such as F(ab')$_2$; single chain Fv (scFv); and Fc fragments. Such terms are described in, for example, Harlow and Lane, *Antibodies: A Laboratory Manual*, Cold Spring Harbor Laboratory, New York (1989); *Molec. Biology and Biotechnology: A Comprehensive Desk Reference* (Myers, R. A. (ed.), New York: VCH Publisher, Inc.); Huston et al., *Cell Biophysics*, 22:189–224 (1993); Plückthun and Skerra, *Meth. Enzymol.*, 178:497–515 (1989) and in Day, E. D., *Advanced Immunochemistry*, Second Ed., Wiley-Liss, Inc., New York, N.Y. (1990), which are incorporated herein by reference. The term functional fragment is intended to include, for example, fragments produced by protease digestion or reduction of a human monoclonal antibody and by recombinant DNA methods known to those skilled in the art.

The term "VL fragment," as used herein, refers to a fragment of the light chain of a human monoclonal antibody which includes all or part of the light chain variable region, including the CDRs. A VL fragment can further include light chain constant region sequences.

The term "Fd fragment," as used herein, refers to a fragment of the heavy chain of a human monoclonal antibody which includes all or part of the heavy chain variable region, including the CDRs. An Fd fragment can further include heavy chain constant region sequences.

The term "Fv fragment," as used herein, refers to a monovalent antigen-binding fragment of a human monoclonal antibody, including all or part of the variable regions of the heavy and light chains, and absent of the constant regions of the heavy and light chains. The variable regions of the heavy and light chains include, for example, the CDRs. For example, an Fv fragment includes all or part of the amino terminal variable region of about 110 amino acids of both the heavy and light chains.

The term "Fab fragment," as used herein, refers to a monovalent antigen-binding fragment of a human monoclonal antibody that is larger than an Fv fragment. For example, an Fab fragment includes the variable regions, and all or part of the first constant domain of the heavy and light chains. Thus, a Fab fragment additionally includes, for example, amino acid residues from about 110 to about 220 of the heavy and light chains.

The term "Fab' fragment," as used herein, refers to a monovalent antigen-binding fragment of a human monoclonal antibody that is larger than a Fab fragment. For example, a Fab' fragment includes all of the light chain, all of the variable region of the heavy chain, and all or part of the first and second constant domains of the heavy chain. For example, a Fab' fragment can additionally include some or all of amino acid residues 220 to 330 of the heavy chain.

The term "F(ab')$_2$ fragment," as used herein, refers to a bivalent antigen-binding fragment of a human monoclonal antibody. A F(ab')$_2$ fragment includes, for example, all or part of the variable regions of two heavy chains and two light chains, and can further include all or part of the first constant domains of two heavy chains and two light chains.

One skilled in the art knows that the exact boundaries of a fragment of a human monoclonal antibody are not important, so long as the fragment maintains a functional activity. Using well-known recombinant methods, one skilled in the art can engineer a nucleic acid to express a functional fragment with any endpoints desired for a particular application.

As used herein, the term "label" is intended to mean a moiety that can be attached to a human monoclonal antibody or other molecule of the invention. Moieties can be used, for example, for therapeutic or diagnostic procedures.

Therapeutic labels include, for example, moieties that can be attached to a molecule of the invention and used to reduce the uncontrolled proliferation or viability of a neoplastic cell. A label which can decrease cell proliferation or viability can be, for example, a cytotoxic or cytostatic agent, growth factor, cell death receptor agonist or immune modulator.

Diagnostic labels include, for example, moieties which can be detected by analytical methods. Analytical methods include, for example, qualitative and quantitative procedures. Qualitative analytical methods include, for example, immunohistochemistry and indirect immunofluorescence. Quantitative analytical methods include, for example, immunoaffinity procedures such as radioimmunoassay, ELISA or Facs analysis. Analytical methods also include both in vitro and in vivo imaging procedures. Specific examples of diagnostic labels that can be detected by analytical means include enzymes, radioisotopes, fluorochromes, chemiluminescent markers, and biotin.

A label can be attached directly to a molecule of the invention, or be attached to a secondary binding agent that specifically binds a molecule of the invention. Such a secondary binding agent can be, for example, a secondary antibody. A secondary antibody can be either polyclonal or monoclonal, and of human, rodent or chimeric origin.

As used herein, the term "cytotoxic or cytostatic agent" is intended to mean an agent which reduces the viability or proliferative potential of a cell. Such agents can be attached, for example, to a human monoclonal antibody or other molecule of the invention and used to target cells or tissues. The targeted cells and tissues can include, for example, neoplastic cells and tumors. Examples of targeted cells and tissues include those derived from breast, lung and ovarian tissue. Cytotoxic or cytostatic agents can function in a variety of ways to reduce cell viability or proliferation. Such functions include, for example, inhibiting DNA synthesis, inhibiting cell division, inducing apoptosis, or inducing non-apoptotic cell killing. Specific examples of cytotoxic and cytostatic agents include pokeweed antiviral protein, abrin, ricin and each of their A chains, doxorubicin, cisplastin, Iodine-131, Yttrium-90, Rhenium-188, Bismuth-212, Taxol, 5-Fluorouracil VP-16, Bleomycin, methotrexate, vindesine, adriamycin, vincristine, vinblastine, BCNU, mitomycin and cyclophosphamide and certain cytokines such as TNF-α and TNF-β. Thus, cytotoxic or cytostatic agents can include, for example, radionuclides, chemotherapeutic drugs, proteins and lectins.

As used herein, the term "specific binding" is intended to mean a selective interaction of a human monoclonal antibody or functional fragment thereof with an antigen. For such an interaction to be selective, a human monoclonal antibody will not substantially bind, or can be made to not substantially bind, to markers other than the particular antigen. Specific binding can include, for example, binding affinity constants of about $10^5$ mol$^{-1}$ to about $10^{12}$ mol$^{-1}$. Specific binding can also include, for example, high avidity interactions.

As used herein, the term "cancer" refers to a pathological condition characterized by the presence of neoplastic cells. Neoplastic cells are cells that exhibit an abnormal morphological or proliferative phenotype. Such cells are characterized by, for example, anchorage independent cell growth, proliferation in reduced-serum medium, and loss of contact inhibition. Such cells are also characterized by, for example, abnormal new growth of tissue, such as a tumor, angiogenic vasculature, and invasion into surrounding tissue. Neoplastic cells can also metastasize from a primary tumor to other sites in the body. For example, a tumor of the breast, lung or ovary can metastasize to other organs yet still be recognizable as being comprised of breast, lung or ovarian cells. Thus, the term "tumor" or "cancer" in reference to breast, lung or ovary is intended to include metastases of these tumors to other organs of the body.

As used herein, the term "effective amount" is intended to mean the amount of a molecule of the invention which can reduce proliferation of neoplastic cells. The actual amount considered to be an effective amount for a particular application can depend, for example, on such factors as the affinity, avidity, stability, bioavailability or selectivity of the molecule, the moiety attached to the molecule, the pharmaceutical carrier and the route of administration. Effective amounts can be determined or extrapolated using methods known to those skilled in the art. Such methods include, for example, in vitro assays with cultured cells or tissue biopsies and credible animal models.

The invention provides a human monoclonal antibody or functional fragment having at least one CDR with substantially the amino acid sequence of a CDR of SEQ ID NO:2 or SEQ ID NO:4. The invention also provides a human monoclonal antibody or functional fragment having at least one CDR with substantially the amino acid sequence of a CDR of SEQ ID NO:6 or SEQ ID NO:8. The invention further provides human monoclonal antibodies or functional fragments thereof produced by the hybridoma cell lines H1140, H2420 and H935. The hybridoma cell lines H1140, H2420 and H935 are also provided.

The human monoclonal antibodies produced by the hybridoma cell lines LH11238, LH13, H1140, H2420 and H935 all exhibit specific binding to neoplastic cells as compared to normal cells and, therefore, are tumor-specific human monoclonal antibodies. In particular, the human monoclonal antibodies of the invention all selectively bind breast carcinoma cells and show relatively little binding to normal fibroblasts. For example, the LH11238 antibody specifically binds to an antigen present on the surface and lysosomal compartments of breast and ovarian carcinoma cells, as compared to normal fibroblasts, peripheral blood lymphocytes, melanoma cells or lung carcinoma cells. The LH13 antibody specifically binds a product produced by breast, lung and ovarian carcinoma cells, as compared to normal fibroblasts and melanoma cells.

The human monoclonal antibodies produced by hybridoma lines H1140, H2420, H935 and LH13 are of the IgM isotype and λ light chain class, whereas human monoclonal antibodies produced by hybridoma line LH11238 is of the IgM isotype and κ light chain class. Further properties of the tumor-specific human monoclonal antibodies are described below in the Examples.

The nucleotide sequence encoding the heavy chain variable region (VH) of the human monoclonal antibody produced by LH11238 cell line has been determined and is designated SEQ ID NO:1. The VH amino acid sequence of the human monoclonal antibody produced by LH11238 cell line is designated SEQ ID NO:2. The nucleotide sequence encoding the light chain variable region (VL) of the human monoclonal antibody produced by LH11238 cell line has also been determined and is designated SEQ ID NO:3. The VL amino acid sequence of the human monoclonal antibody produced by LH11238 cell line is designated SEQ ID NO:4.

The nucleotide sequence encoding the heavy chain variable region (VH) of the human monoclonal antibody produced by LH13 cell line has been determined and is designated SEQ ID NO:5. The VH amino acid sequence of the human monoclonal antibody produced by LH13 cell line is designated SEQ ID NO:6. The nucleotide sequence encoding the light chain variable region (VL) of the human monoclonal antibody produced by LH13 cell line has also been determined and is designated SEQ ID NO:7. The VL amino acid sequence of the human monoclonal antibody produced by LH13 cell line is designated SEQ ID NO:8.

The hybridomas producing the tumor-specific human monoclonal antibodies of the invention were generated by in vitro immunization of human spleen cell cultures with breast carcinoma cells. Briefly, a mixed lymphocyte reaction (MLR) was established by co-culturing single cell suspensions isolated from allogeneic human spleens. Tumor-reactive lymphocytes were subsequently enriched by incubating MLR cultures either with monolayers or with enriched plasma membranes of breast carcinoma cells. In order to provide a permanent source of human monoclonal antibodies of the invention, immunized lymphocytes were immortalized either by fusion with the K6H6/B5 heteromyeloma cell line or by transformation with EBV followed by fusion with K6H6/B5 cells. The particular source of antigen and the immortalization procedures used to generate each of the hybridoma cell lines of the invention are described more fully below in the Examples.

The tumor-specific human monoclonal antibodies of the invention can also be generated by methods known to those skilled in the art. These methods include, for example, in vivo and in vitro enrichment of tumor-reactive lymphocytes. For example, an individual with a breast, lung or ovarian tumor can possess lymphocytes which express antibodies that specifically bind tumor-specific antigens, including, for example, LH13, LH11238, H1140, H2420 or H935 antigens. Such lymphocytes can be isolated, for example, from the peripheral blood or from the spleen of the patient, and immortalized as described below.

Methods are also well known in the art for in vitro enrichment of tumor-reactive human lymphocytes, using tumor-specific antigens. The source of antigen can be, for example, substantially pure antigen, tumor cells or tumor cell fractions. A substantially pure antigen can be prepared by any of the methods well known to those skilled in the art, including, for example, chromatography, electrophoretic separation and immuno-isolation.

An antigen useful for preparing human monoclonal antibodies of the invention can be, for example, neoplastic cells.

The neoplastic cells can be, for example, cells obtained directly from tumors, cultured primary tumor cells or established cell lines. Such cells can originate from any organ, tissue or fluid of the body, including, for example, breast, lung or ovary. The cancer cells can be untreated, fixed or growth-arrested. The fixation can be by any number of methods known to those skilled in the art, including, for example, chemical fixation. Useful chemicals for fixation include, for example, paraformaldehyde, glutaraldehyde, methanol, or acetone. The cells can alternatively be growth-arrested using cytostatic agents. A specific example of a cytostatic agent is mitomycin C.

An antigen useful for preparing human monoclonal antibodies of the invention can also be a fraction of tumor cells. The tumor cell fraction can be, for example, cellular membranes, cytoplasmic contents, or nuclei. Methods for cell fractionation are well known in the art. An antigen for preparing monoclonal antibodies of the invention can also be an antigen secreted by tumor cells. Such an antigen can be prepared, for example, by isolation of conditioned medium or cell matrix of tumor cells using procedures known in the art.

An antigen prepared as described above can be used to stimulate human lymphocytes to generate the tumor-specific human monoclonal antibodies of the invention. Human lymphocytes can be obtained, for example, from the peripheral blood of live individuals, or from the spleen of individuals who are deceased or undergoing surgery. Lymphocytes can be cultured with antigen directly. Alternatively, lymphocytes can be cultured with antigen in a mixed lymphocyte reaction in the presence of allogeneic lymphocytes. Appropriate culturing conditions for a particular antigen and lymphocyte source can readily be determined by those skilled in the art.

If desired, antigen-primed lymphocytes enriched by in vivo or in vitro stimulation as described above can be immortalized by any of a number of procedures known to those skilled in the art. Immortalization provides a permanent source of tumor-specific human monoclonal antibodies. Immortalization of lymphocytes can be accomplished by, for example, fusion with an immortal cell line. Such immortal cell lines useful for cell fusion can be, for example, human myeloma cells or human lymphoblastoid B cell lines. Fusion partners can also be rodent myeloma cells or human:rodent heteromyeloma cell lines. The heteromyeloma cell line can be, for example, the human:mouse heterohybridoma cell line K6H6/B5. Alternatively, antigen-primed lymphocytes can be immortalized by viral transformation, using, for example, viruses. A useful virus for immortalization by viral transformation is EBV. Antigen-primed lymphocytes can also be immortalized by viral transformation followed by fusion. Viral transformation followed by fusion can be, for example, EBV transformation followed by fusion with the K6H6/B5 cell line. Culture conditions for lymphocyte fusion or viral transformation can readily be determined by those skilled in the art.

Immortalized lymphocytes can be screened for the production of human monoclonal antibodies that specifically bind to human tumor cells using immunoassays known to those skilled in the art. Such immunoassays include, for example, quantitative and qualitative immunoassays. Qualitative immunoassays include, for example, precipitin methods, agglutinin reactions, immunohistochemistry, immunofluorescence, immunoblotting and immunoprecipitation. Quantitative immunoassays include, for example, immunoaffinity methods such as radioimmunoassay, Facs analysis, and ELISA analysis. ELISA analysis can be direct, sandwich or competitive. Immunoassays can be direct, using, for example, a labeled human monoclonal antibody. Such methods can alternatively be indirect, using, for example, a labeled anti-human secondary antibody. The label can be, for example, a fluorescent label, an enzyme, a radioisotope, or biotin. Detection can be by spectrophotometric, radiographic or chemiluminescent means, depending on the immunoassay.

The tumor-specific antigen sample used for screening monoclonal antibodies for tumor reactivity need not be the same as the antigen sample used to immunize the human lymphocytes. The antigen used in screening can be, for example, substantially purified antigen, live or fixed tumor cell monolayers, live or fixed tumor cell suspensions, fractions of tumor cells, or sections of tumor biopsies, depending on the assay procedure employed. The tumor cells can be, for example, human breast, ovarian or lung carcinoma cells.

The tumor-specific human monoclonal antibodies of the invention do not bind, bind only minimally, or can be made to bind only minimally to normal cell antigens. Normal cells or fractions of normal cells can be used as controls for screening human monoclonal antibodies. Such normal cells can be, for example, live or fixed normal tissues or cultured cell lines. Cultured normal cell lines that can be used as controls include, for example, human fibroblasts and peripheral blood lymphocytes. Although any normal cell can be used as a control, the selection of a particular control will be based, in part, on the specificity of the particular tumor-specific monoclonal antibody which is being screened. For example, if a human tumor-specific monoclonal antibody is produced and screened against a carcinoma cell, then one type of normal cell which can be used as a comparison is a normal epithelial cell culture or cell line. Similarly, if a human tumor-specific monoclonal antibody is produced and screened against a sarcoma cell, then one type of normal cell which can be used as a comparison is a normal fibroblast cell culture or cell line. A normal cell culture or cell line from the same tissue type or from the same individual can also provide a normal control. Those skilled in the art will know what is an appropriate type of normal cell to be used as a control to determine specific binding to a particular type of tumor cell.

Tumor-specific human monoclonal antibodies can be purified and quantitated for use in immunodiagnostic and immunotherapeutic procedures. Such purification methods are well known to those skilled in the art and depend on the source of human monoclonal antibodies and the particular application. Purification methods can include, for example, precipitation, electophoresis, chromatography, and immunoaffinity purification. The purified antibodies can be quantitated in comparison with known standard controls, using, for example, spectrophotometry or immunoassays known in the art.

To further characterize tumor-specific human monoclonal antibodies, their class and subclass can also be determined by immunoassays that measure the presence of individual heavy and light chain polypeptides. Such immunoassays include ELISA assays and are known to those skilled in the art.

The invention further provides functional fragments of the tumor-specific human monoclonal antibodies of the invention. A functional fragment of a human monoclonal antibodies maintains a biological activity, such as specific binding or an effector function. A functional fragment can therefore be beneficially used for the detection and treatment of cancer.

Functional fragments include fragments with substantially the same heavy and light chain variable regions as a tumor-specific human monoclonal antibody of the invention. For example, functional fragments include fragments wherein at least one of the CDR sequences consist of substantially the same amino acid sequence as the CDR sequences of a tumor-specific human monoclonal antibody of the invention. Such functional fragments include, for example, VL, Fd, Fv, Fab, Fab', F(ab')$_2$ and Fc fragments. For example, a functional fragment could have one or more of the three CDR sequences of the VL, or one or more of the three CDR sequences of the VH, or a combination of VL and VH CDRs of a human monoclonal antibody of the invention. The appropriate number and combination of VH and VL CDR sequences can be determined by those skilled in the art depending on the desired affinity and specificity and the intended use of the functional fragment.

Functional fragments of human monoclonal antibodies of the invention can readily be produced and isolated using methods well known to those skilled in the art. Such methods include, for example, proteolytic methods, recombinant methods and chemical synthesis. Proteolytic methods for the isolation of functional fragments use human monoclonal antibodies as starting material. Enzymes suitable for proteolysis of human monoclonal antibodies include, for example, papain, pepsin and elastin. The appropriate enzyme can be readily chosen by one skilled in the art, depending on, for example, whether monovalent or bivalent fragments are required. For example, papain cleavage results in two monovalent Fab' fragments that bind antigen and an Fc fragment. Pepsin cleavage, for example, results in a bivalent F(ab')$_2$ fragment. A F(ab')$_2$ fragment of the invention can further be reduced using, for example, DTT or β-mercaptoethanol to produce two monovalent Fab' fragments.

Functional fragments produced by proteolysis can be purified by affinity and column chromatographic procedures. For example, undigested antibodies and Fc fragments can often be removed by binding to protein A. Additionally, functional fragments can be purified by virtue of their charge and size, using, for example, ion-exchange and gel filtration chromatography. Such methods are well known to those skilled in the art.

Recombinant methods for producing functional fragments of human monoclonal antibodies begin with the isolated nucleic acid of desired regions of the immunoglobulin heavy and light chains. Such regions can include, for example, all or part of the variable region of the heavy and light chains. Such regions can particularly include the CDRs of the heavy and light chains.

The invention provides an isolated nucleic acid encoding a human monoclonal antibody or functional fragment thereof, comprising a nucleotide sequence encoding substantially the amino acid sequence of at least one CDR encoded by SEQ ID NO:1 or SEQ ID NO:3. Also provided is an isolated nucleic acid encoding a CDR, comprising substantially the amino acid sequence of a CDR encoding by SEQ ID NO:1 or SEQ ID NO:3. The invention further provides an isolated nucleic acid encoding a human monoclonal antibody or functional fragment thereof, comprising a nucleotide sequence encoding substantially the amino acid sequence of at least one CDR encoded by SEQ ID NO:5 or SEQ ID NO:7. Also provided is an isolated nucleic acid encoding a CDR, comprising substantially the amino acid sequence of a CDR encoding by SEQ ID NO:5 or SEQ ID NO:7.

A nucleic acid encoding a human monoclonal antibody or functional fragment of the invention can be produced using methods known to those skilled in the art. One useful procedure for isolating such DNA begins with cDNA which can be reverse-transcribed from RNA of hybridoma cells that produce a tumor-specific human monoclonal antibody. Methods for cDNA synthesis are well known in the art. A cDNA encoding a functional fragment of a heavy or light chain can be amplified using, for example, the polymerase chain reaction (PCR). The PCR technology is the subject matter of U.S. Pat. Nos. 4,683,195, 4,800,159, 4,754,065, and 4,683,202, all of which are incorporated by reference herein. Suitable primers for PCR are known and can be determined by those of skill in the art using conserved sequences which flank the particular functional fragment of a heavy or light chain. Suitable PCR conditions are known and can also similarly be determined by those skilled in the art.

A nucleic acid encoding a functional fragment of a human monoclonal antibody of the invention can also be directly synthesized by methods of oligonucleotide synthesis known in the art. Alternatively, smaller fragments can be synthesized and joined to form a larger functional fragment using recombinant methods known in the art.

Nucleic acids encoding a functional fragment of a human monoclonal antibody of the invention can be cloned into a suitable expression vector and expressed in a suitable host. A suitable vector and host cell system can allow, for example, co-expression and assembly of functional fragments of the heavy and light chains. Suitable systems for the expression of antibody fragments can be determined by those skilled in the art and include, for example, M13 phage immunoexpression vectors. Recombinant functional fragments of the invention can be substantially purified using methods known in the art, and which depend on the particular vector and host expression system used.

Isolated nucleic acids encoding tumor-specific human monoclonal antibodies or functional fragments can also be engineered to produce antibodies with optimal properties such as affinity, selectivity, avidity, stability or bioavailability. Such modifications can include, for example, addition, deletion, or substitution of amino acid residues or substitution of a D-amino acid or amino acid mimetic, so long as the fragment maintains a functional activity such as, for example, antigen binding specificity.

Amino acid substitutions can be introduced by mutating nucleic acid codons encoding the particular amino acid using methods known in the art. Single or multiple codons can be varied, so long as the fragment retains a functional activity. Rapid methods for making and screening multiple simultaneous changes are well known within the art and can be used to produce a library of encoding nucleic acids which contain all possible or all desired changes and then expressing and screening the library for human monoclonal antibodies or fragments which retain function. Such methods include, for example, codon based mutagenesis, synthesis of stochastic oligonucleotides and partially degenerate oligonucleotide synthesis.

Codon based mutagenesis is the subject matter of U.S. Pat. Nos. 5,264,563 and 5,523,388 and is advantageous for the above procedures since it allows for the production of essentially any and all desired frequencies of encoded amino acid residues at any and all particular codon positions within an oligonucleotide. Such desired frequencies include, for example, the truly random incorporation of all twenty amino acids or a specified subset thereof as well as the incorporation of a predetermined bias of one or more particular amino acids so as to incorporate a higher or lower frequency of the biased residues compared to other incorporated amino acid residues.

Synthesis of stochastic oligonucleotides and partially degenerate oligonucleotide synthesis can similarly be used for producing and screening for functionally equivalent amino acid changes. However, due to the degeneracy of the genetic code, such methods can incorporate redundancies at a desired amino acid position (see, for example, U.S. Pat. No. 5,723,323). Stochastic oligonucleotide synthesis includes the coupling of all four nucleotides at each nucleotide position within a codon. Other stochastic methods of synthesis also exist which can result in degenerate or partially degenerate oligonucleotides or oligonucleotides which encode completely random amino acid sequences (see, for example, U.S. Pat. No. 5,723,323).

Partially degenerate oligonucleotide synthesis is the coupling of equal portions of all four nucleotides at the first two nucleotide positions, for example, and equal portions of two nucleotides at the third position. Both of these latter synthesis methods can be found described in, for example, Cwirla et al., *Proc. Natl. Acad. Sci. USA* 87:6378–6382, (1990) and Devlin et al., *Science* 249:404–406, (1990).

For certain therapeutic and diagnostic applications it may be preferable to use antibodies with the same antigen specificity but with different isotypic or allotypic determinants. Such antibodies could have, for example, decreased immunogenicity, increased stability, or more optimal effector functions. Thus, functional fragments of the invention can include those obtained by cloning the CDR sequences of a human monoclonal antibody of the invention into different framework regions. Such different framework regions can be obtained from different species, different human individuals, or different heavy or light chain classes from the same or different individual. Such CDR grafting methods are well known to those skilled in the art.

Functional activity of fragments of the invention can be evaluated by, for example, methods described above for determining the immunoreactivity of human monoclonal antibodies. Particularly useful methods for determining functional activity of fragments include competitive radioimmunoassay and competitive ELISA assay.

The present invention provides pharmaceutical compositions containing a human monoclonal antibody or functional fragment of the invention and a pharmaceutical carrier. Such compositions can be used to administer a human monoclonal antibody or fragment to reduce the proliferation or viability of neoplastic cells. Such compositions can also be used to detect neoplastic cells.

Suitable pharmaceutical carriers for the methods of the invention are well known and include, for example, aqueous solutions such as physiologically buffered saline, and other solvents or vehicles such as glycols, glycerol, oils or injectable organic esters. A pharmaceutical carrier can contain a physiologically acceptable compound that acts, for example, to stabilize or increase the solubility of a pharmaceutical composition. Such a physiologically acceptable compound can be, for example, a carbohydrate, such as glucose, sucrose or dextrans; an antioxidant, such as ascorbic acid or glutathione; a chelating agent; a low molecular weight protein; or another stabilizer or excipient. Pharmaceutical carriers, including stabilizers and preservatives, are described, for example, in Martin, *Remington's Pharm. Sci.*, 15th Ed. (Mack Publ. Co., Easton, 1975), which is incorporated herein by reference.

Those skilled in the art will know that the choice of the pharmaceutical medium and the appropriate preparation of the composition will depend on the intended use and mode of administration.

The invention also provides a CDR or functional fragment thereof having substantially the amino acid sequence of a CDR of SEQ ID NO:2 or SEQ ID NO:4. The invention also provides a CDR or functional fragment thereof, having substantially the amino acid sequence of a CDR of SEQ ID NO:6 or SEQ ID NO:8.

A CDR or functional fragment thereof of the invention can be produced by methods known in the art and as described above. For example, a CDR of the invention can be produced by recombinant means or chemical synthesis. A CDR of the invention can be advantageously used, for example, to generate anti-idiotypic antibodies that selectively bind the tumor-specific human monoclonal antibodies of the invention. Methods for producing and using anti-idiotypic antibodies for diagnostic and therapeutic purposes are well known in the art.

The invention further provides a method of reducing neoplastic cell proliferation by administering to the cell an effective amount of a human monoclonal antibody or functional fragment produced by a cell line selected from the group consisting of H1140, H2420 and H935. Also provided is a method of reducing neoplastic cell prolieration by administering to the cell an effective amount of a human monoclonal antibody or functional fragment having at least one CDR with substantially the amino acid sequence of a CDR of SEQ ID NO:2 or SEQ ID NO:4. Further provided is a method of reducing neoplastic cell proliferation by administering to the cell an effective amount of a human monoclonal antibody or functional fragment having at least one CDR with substantially the amino acid sequence of a CDR of SEQ ID NO:6 or SEQ ID NO:8. A human monoclonal antibody or functional fragment used for reducing neoplastic cell proliferation can further include a label, such as a cytotoxic or cytostatic agent, and can be combined with a pharmaceutical carrier.

An effective amount of a molecule of the invention for reducing neoplastic cell proliferation is known or can readily be determined by one skilled in the art using in vitro methods or credible animal models. In vitro methods can include, for example, determining an effective amount of a composition for reducing neoplastic cell growth or neoplastic cell metastasis. A neoplastic cell used in an in vitro method for assaying reduction in growth or metastasis can be, for example, a tumor cell line or an ex vivo culture of a tumor. The cell line or tumor can be, for example, of breast, lung or ovarian tissue in origin. An effective amount for inhibiting neoplastic cell growth can be, for example, an effective amount for inhibiting DNA synthesis, inhibiting cell division, inducing apoptosis, inducing non-apoptotic killing, or inhibiting angiogenesis. An effective amount for inhibiting metastasis of a neoplastic cell can be, for example, an amount effective for inhibiting cell motility, cell migration, cell attachment, cell invasion or cell proliferation.

An effective amount of a molecule of the invention for reducing neoplastic cell proliferation can also be determined from xenografts of human tumors in rodents. The rodent can be, for example, a rat or a mouse. The mouse can be, for example, normal or immunocompromised. An immunocompromised mouse can be, for example, a nude mouse or a scid mouse. Such species are well known in the art and can be obtained from commercial sources. Human cancer cells can be introduced into an animal by a number of routes, including subcutaneously, intraveneously and intraperitoneally. Following establishment of a tumor, the animals can be treated with different doses of a molecule of the invention, and tumor mass or volume can be determined. Efficacy can be measured as partial or complete regression of the tumor.

An effective dose for treating cancer results in more partial and complete regressions of tumors.

An effective amount of a molecule of the invention can be determined by one skilled in the art and will depend on such factors as age, body weight, sex and medical condition of the individual, and the particular route of administration of the therapeutic agent. Useful routes of administration of a composition of the invention for treating cancer include, for example, intramuscular, intratumoral, intravascular, intraperitoneal, subcutaneous or intranasal routes.

The efficacy of a particular treatment in cancer patients can be determined by one skilled in the art. For example, in vivo or in vitro diagnostic methods, such as those described below, can be used to determine that a tumor has regressed or been eliminated following treatment. Additionally, normal prognostic indicators, such as survival and increased quality of life for the cancer patient, can be used.

The invention provides a method of detecting neoplastic cells by contacting a sample with a human monoclonal antibody or functional fragment produced by a cell line selected from the group consisting of H1140, H2420 and H935, and detecting the specific binding of the human monoclonal antibody or functional fragment to the sample, wherein the presence or increased level compared to a normal cell of the human monoclonal antibody or functional fragment indicates the presence of or predisposition to cancer. The invention also provides a method of detecting neoplastic cells by contacting a sample with a human monoclonal antibody or functional fragment having substantially the amino acid sequence of a CDR of SEQ ID NO:2 or SEQ ID NO:4, and detecting the specific binding of the human monoclonal antibody or functional fragment to the sample, wherein the presence or increased level compared to a normal cell of the human monoclonal antibody or functional fragment indicates the presence of or predisposition to cancer. The invention further provides a method of detecting neoplastic cells by contacting a sample with a human monoclonal antibody or functional fragment having substantially the amino acid sequence of a CDR of SEQ ID NO:6 or SEQ ID NO:8, and detecting the specific binding of the human monoclonal antibody or functional fragment to the sample, wherein the presence or increased level compared to a normal cell of the human monoclonal antibody or functional fragment indicates the presence of or predisposition to cancer.

As used herein, the term "sample" is intended to mean any biological fluid, cell, tissue, organ or portion thereof, that includes or potentially includes neoplastic cells. A biological fluid can be, for example, blood or lymph. A tissue can be, for example, breast, ovary, or lung. The sample can be an in vivo or in vitro sample. An in vitro sample can be, for example, a histologic section, a specimen obtained by biopsy, or cells that are placed in or adapted to tissue culture. A sample can be prepared by methods known in the art suitable for the particular format of the detection method.

A sample can be contacted with a human monoclonal antibody or functional fragment of the invention and specific binding of the human monoclonal antibody to the sample can be detected. Such contacting can be in vivo or in vitro, as determined by one skilled in the art depending on the format of the detection method used. Specific binding of the human monoclonal antibody to the sample can be determined by immunoassays as described above. Such immunoassays include, for example, both in vivo and in vitro immunoassays. In vivo immunoassays include, for example, radioimaging. Such a method involves contacting a sample within an individual with a monoclonal antibody of the invention, and detecting specific binding by, for example, radiographic imaging. In vitro immunoassays include both qualitative and quantitative assays, such as, for example, immunohistochemistry, immunofluorescence, radioimmunoassay, Facs analysis, immunoblotting, immunoprecipitation and ELISA analysis, as described above.

The determination that neoplastic cells are present can be made by determining that a specifically bound human monoclonal antibody of the invention is present or is at an increased level compared to a normal cell. As described above, one skilled in the art would be able to determine an appropriate normal cell to use for comparison with a particular type of neoplastic cell.

The invention further provides a substantially pure human tumor-specific antigen. The term "tumor-specific antigen" is intended to mean an antigen which is preferentially expressed by human tumor cells. The term "preferentially expressed by human tumor cells" is intended to mean that a tumor-specific antigen is expressed by human tumor cells and is expressed at a substantially lower level by normal human cells. Such tumor cells that express a tumor-specific antigen of the invention can be, for example, of breast, lung or ovarian tissue origin.

A human tumor-specific antigen of the invention is specifically reactive with a human monoclonal antibody of the invention. Such an antigen can specifically react with, for example, a human monoclonal antibody or functional fragment produced by LH11238, LH13, H1140, H2420 or H935 hybridoma cell lines. Such an antigen can also specifically react with a human monoclonal antibody or functional fragment having at least one CDR with substantially the amino acid sequence of a CDR of SEQ ID NO:2 or SEQ ID NO:4, or with a human monoclonal antibody or functional fragment having at least one CDR with substantially the amino acid sequence of a CDR of SEQ ID NO:6 or SEQ ID NO:8. The antigen reactive with LH11238 human monoclonal antibody is a protein present on the cell surface and in lysosomal compartments of breast and ovarian cancer cells as compared to normal human fibroblasts, peripheral blood lymphocytes, melanoma cells or lung carcinoma cells. The antigen reactive with LH13 human monoclonal antibody is a secreted glycoprotein produced by breast, lung and ovarian cancer cells as compared to normal fibroblasts or melanoma cells. Further properties of LH11238 and LH13 antigens are described in the Examples.

Human tumor-specific antigens of the invention can beneficially be used for the treatment and diagnosis of cancer. For example, such antigens can be used to generate additional binding agents that specifically bind the human tumor-specific antigen for use in therapeutic and diagnostic procedures. Such binding agents can, for example, inhibit or stimulate the function of a tumor-specific antigen, or modulate the immune system, such that a neoplastic cell is growth-arrested or killed. Such binding agents can also be conjugated to a label, such as, for example, a cytotoxic or cytostatic agent, that causes the death or arrest of the tumor cells. Useful agents that bind to a tumor-specific antigen of the invention include, for example, ligands, receptor antagonists and antibodies.

A substantially pure tumor-specific antigen can also be used in the treatment of cancer by vaccinating a patient having cancer, or at risk of developing cancer with an effective amount of the antigen. Following vaccination, the immune system of the individual will be able to prevent, reduce the proliferation of, or eliminate neoplastic cells expressing such an antigen.

A substanially pure tumor-specific antigen of the invention can also be beneficially used in methods for detecting binding of a tumor-specific binding agent, such as a human monoclonal antibody or functional fragment of the invention. For example, such an antigen can be used in an immunoassay such as competitive ELISA.

An appropriate starting material for isolating a substantially pure antigen of the invention can be identified by, for example, screening a panel of human tumor cells, using immunoaffinity procedures well known in the art. For example, as described in Example II, ELISA analysis can be used to determine a useful cell source of antigen for subsequent purification. A useful cell source of antigen can be, for example, breast, ovarian, or lung carcinoma. A particularly useful starting material for the purification of a tumor-specific antigen is the H3396 breast carcinoma cell line.

An appropriate method for isolating a substantially pure antigen depends on the cellular localization of the antigen. For example, an antigen of the invention can be predominantly expressed in the secreted medium, cell surface membrane, vesicular membranes, cytoplasm, or nucleus of the neoplastic cell. Cellular localization of an antigen can be determined by, for example, immunoassays well known in the art. For example, as described in Examples IV and VI, indirect immunofluorescence and ELISA analysis can be used to establish the predominant localization of an antigen.

Purification of an antigen can be monitored by immunoaffinity procedures known in the art. Particularly useful methods of monitoring purification include, for example, ELISA analysis and immunoblotting.

Tumor-specific antigens can be purified from a particular source by biochemical procedures well known in the art. For example, purification can include centrifugation, chromatographic methods, electrophoretic methods and immunoaffinity methods, and can be chosen by one skilled in the art depending on the characteristics of a particular antigen. Centrifugation procedures can be used to concentrate or enrich for a subcellular fraction which contains an abundant amount of the antigen. Such subcellular fractionation procedures are well known in the art. Chromatographic methods are also well known in the art, and include methods of separating an antigen from contaminants based on its size or differential affinity for particular resins. Such resins can include, for example, size exclusion resins, ion exchange resins, and lectin columns. As described in Example VI, a particularly useful resin for purification of an antigen of the invention is Q SEPHAROSE FAST FLOW agarose resin. Electrophoretic methods are also well known in the art, and include one and two-dimensional electrophoresis through, for example, acrylamide or agarose gels. Immunoaffinity procedures are also well known in the art and include compounds conjugated to a human monoclonal antibody of the invention. Useful compounds for conjugating an antibody for immunoaffinity purification of a tumor-specific antigen include chromatographic resins and Protein A.

Thus, following well-known biochemical procedures, one skilled in the art can readily isolate a substantially pure tumor-specific antigen of the invention for use in therapeutic and diagnostic procedures.

Substantially purified tumor-specific antigens of the invention can also be prepared from nucleic acids encoding tumor-specific antigens of the invention by recombinant methods known to those skilled in the art.

The invention provides isolated nucleic acids encoding human tumor-specific antigens. Nucleic acids encoding human tumor-specific antigens can be isolated by methods known to those skilled in the art. Such methods include, for example, using monoclonal antibodies of the invention to screen an expression library. Other methods include, for example, screening a cDNA or genomic library using degenerate oligonucleotides as hybridization probes. The sequence of such a degenerate oligonucleotide can be determined by microsequencing an isolated tumor-specific antigen of the invention or fragment thereof.

Other methods known to those skilled in the art for producing a nucleic acid of a tumor-specific antigen include, for example, the polymerase chain reaction (PCR), using degenerate oligonucleotide primers obtained from amino acid sequence of a tumor-specific antigen of the invention. Desired sequences can be amplified exponentially starting from as little as a single gene copy by means of PCR.

The above described methods are known to those skilled in the art and are described, for example, in Sambrook et al., *Molecular Clonina: A Laboratory Manual*, Cold Spring Harbor Laboratory, New York (1992) and the various references cited therein and in Ansubel et al., *Current Protocols in Molecular Biology*, John Wiley and Sons, Baltimore, Md. (1989); and in Harlow et al., *Antibodies: A Laboratory Manual*, Cold Spring Harbor Laboratory, New York (1989). These references and the publications cited therein are hereby expressly incorporated by reference.

It is understood that modifications which do not substantially affect the activity of the various embodiments of this invention are also included within the definition of the invention provided herein. Accordingly, the following examples are intended to illustrate but not limit the present invention.

EXAMPLE I

Production of Tumor-specific Human Monoclonal Antibodies

This Example shows production of hybridomas that secrete human monoclonal antibodies specifically reactive with tumor cells. A procedure for immunizing normal lymphocytes in vitro with tumor cells or cell membranes prior to immortalization is described. This procedure allowed enrichment of lymphocytes producing novel tumor-reactive human monoclonal antibodies. These human monoclonal antibodies will be useful for cancer immunotherapeutic and immunodiagnostic procedures.

Lymphocytes were prepared as follows. Spleen tissue was isolated from accident victims, fragmented, and forced through a no. 50 mesh wire screen (Bellco, Vineland, N.J.). Th e cells were collected by centrifugation at 250×g for 10 min and RBC were removed by ammonium chloride lysis. The remaining cells were washed, resuspended in freezing medium (40% RPMI, 50% FCS and 10% DMSO) at a concentration of 100 to 300×$10^6$ cells/ml, frozen in 1.5-ml aliquots, and stored in liquid nitrogen. Both adherent cells and lymphocytes were isolated by this procedure.

A mixed lymphocyte reaction (MLR) was then established as follows. Frozen single-cell splenocyte preparations (described above) from two different donors were thawed by gentle shaking at 37° C., washed twice with RPMI, and collected by centrifugation for 10 min at 250×g. After the second wash, 3×$10^6$ splenocytes from each of the sources were combined in 2 ml of RPMI containing 1.5 mM HEPES, pH 7.4 (Fisher Scientific), 10% FBS (HyClone), 2 mM L-glutamine, non-essential amino acids, 1 mM sodium pyruvate, and 100 µg/ml gentamicin sulfate and placed in a 24-well tissue culture dish. This MLR, together with antigenic stimulation (described below), endogenously produced the required lymphokines.

MLR cultures were then stimulated with either mitomycin-treated H3396 tumor cells, plasma membrane preparations from H3396 cells, or paraformaldehyde-fixed H3922 tumor cells. H3922 and H3396 are cultured cell lines established from metastases of human breast adenocarcinoma, which were explanted and maintained in culture. Each cell line was derived from a different explant.

Mitomycin-treated H3396 cells were prepared as follows. H3396 cells were plated in 24-well culture dishes, grown to confluency, and treated for 12–15 h with 0.1 µg/ml mitomycin C. This concentration arrested cell division in the tumor cell lines for approximately seven days. Following the 12–15 h incubation, the mitomycin C-containing media was removed and the cells were washed three times with 2 ml of phosphate buffered saline (PBS).

Paraformaldeyde-fixed H2922 tumor cells were prepared by incubating cells for 15 min at 25° C. in 2% paraformaldehyde in PBS after removing the culture medium. The cells were then washed four times with PBS prior to use.

Plasma membranes from H3396 cells were isolated as follows. Ten confluent 150-mm dishes of H3396 cells were each rinsed twice with 10 ml of ice-cold (Tris-buffered saline) TBS and harvested in 2 ml/150-mm dish of (Tris saline) TS containing 1 µg/ml leupeptin, 1 µg/ml pepstatin, and 2 mM AEBSF. The cells were broken in a 15 ml Dounce homogenizer with 40 strokes using a type A pestle. The lysate was centrifuged at 800×g at 4° C. for 5 min to remove unbroken cells and nuclei. The supernatant was saved and the pellet was resuspended in 0.5 volumes of TS buffer, homogenized and centrifuged at 800×g. The supernatant was combined with the first supernatant and centrifuged at 10,000×g at 4° C. for 2 h. The supernatant was discarded and the pellet was resuspended in 2 ml of water. A 2 ml Dounce and type B pestle was used to resuspend the membrane pellet. Phase separation of membranes in a 6.4% polymer system was performed on ice by mixing 2.56 ml of 20% dextran, 1.28 ml of 40% polyethylene glycol, 0.20 ml of 0.2 M potassium phosphate, pH 7.2, 0.8 ml of 1 M sucrose, and 2.16 ml of water. To this mixture 1 ml of membranes were added and the tube was inverted 20 times end over end. The phases were separated by centrifugation at 800×g at 4° C. for 5 min. The upper phase was drawn off and mixed with the lower phase recovered from a blank (water) sample. Likewise, the lower phase, including the material at the interface, was mixed with the upper phase recovered from a blank sample. Both phases were mixed, inverted 20 times end over end, and separated by centrifugation at 800×g at 4° C. for 5 min. The material recovered from the upper phase of both samples was combined, the volume was adjusted to 21 ml with TBS, and the membranes were collected by centrifugation at 100,000×g at 4° C. for 2 h. The supernatant was discarded and the pellet was resuspended with a 2 ml Dounce homogenizer with a B pestle in 1–2 ml of TS buffer containing the protease inhibitors. The membranes were stored at 4° C. for 12 h, at which time the insoluble material was separated from the supernatant by centrifugation at 800×g at 4° C. for 10 min. The pellet was suspended a second time in 1–2 ml of TS buffer containing protease inhibitors and stored as a suspension at 4° C. The supernatant is referred to as fraction 1 while the resuspended particulate material is referred to as fraction 2. Plasma membranes in fraction 1 were enriched greater than 10-fold as determined by measuring 5'-nucleotidase or phosphodiesterase activity. The preparations had minimal succinate-dependent cytochrome C reductase (mitochondria), or NADPH-dependent cytochrome C reductase (endoplasmic reticulum) activity.

MLR cultures were immunized in vitro by incubation for three days with one of the following: monolayers of mitomycin C-treated H3396 cells, monolayers of paraformalehyde-fixed H3922 cells, 5 mg of plasma membrane fraction 1 from H3396 cells, or with 10 mg of plasma membrane fraction 2 from H3396 cells.

In vitro immunized lymphocytes were immortalized by either of two alternative methods. In the first method, lymphocytes were fused with K6H6/B5 heteromyeloma cells. K6H6/B5 cells were maintained in spinner culture in a 1:1 mixture of RPMI and Iscoves's modification of DMEM, supplemented with 10% FCS, 1% nonessential amino acids, 2 mM glutamine, and 1 mM sodium pyruvate. Approximately $4 \times 10^6$ lymphocytes were combined with $2 \times 10^6$ log phase K6H6/B5 cells and washed twice with RPMI. One ml of a mixture of 35% polyethylene glycol (approximate m.w. 1450) and 7.5% DMSO in RPMI was added over 1 min, then gradually diluted with RPMI to 4 ml and then diluted with RPMI supplemented with 10% FCS to 16 ml. The lymphocyte concentration was then adjusted to $5 \times 10^4$ cells/ml, and 0.2 ml of cells were seeded in 96-well cell culture dishes in hybridoma medium (RPMI supplemented with 10% FCS, 1% nonessential amino acids, 2 mM glutamine, 1 mM sodium pyruvate, 15 mM HEPES, pH 7.4 and 0.1 mg/ml gentamycin) containing HAT (13.6 µg/ml hypoxanthine, 3.8 µg/ml thymidine, 1 µg/ml azaserine) and 1.0 µM ouabain, to select against unfused cells.

Hybridomas were screened for reactivity as described below, and clones of interest were expanded. Using this one-step immortalization method, 10–50 hybridomas were produced per $10^6$ lymphocytes fused; however, only 5% of the interesting clones were stable through three rounds of cell culturing. Hybridoma clones H1140, H2420 and H935 were obtained by this immortalization procedure.

In an effort to improve clonal stability, a second, two-step method for immortalizing in vitro immunized lymphocytes was evaluated, involving first transforming cells with EBV and then fusing clones of interest with K6H6/B5 heteromyeloma cells. Equal volumes of lymphocytes ($8 \times 10^4$ cells/ml) and EBV-transformed 1A2/C7 cells ($2 \times 10^6$ cells/ml) were combined and the total volume was doubled by the addition of hybridoma medium. Hypoxanthine, thymidine and azaserine were added such that their final concentrations were 13.6 µg/ml, 3.8 µg/ml, and 1 µg/ml, respectively. Two hundred microliters of the mixture of cells was plated per well in 96-well cell culture dishes to yield a final total of 4000 lymphocytes and $1 \times 10^5$ 1A2/C7 cells per well. The cells were fed with hybridoma medium-HAT every three days and assayed for antibody production (described below) after 2 weeks when colonies of cells were visible.

Transformation of lymphocytes with EBV generated a higher percentage of antibody-secreting clones than was obtained from fusions of lymphocytes with the heteromyeloma line (50–100 antibody-secreting clones per $10^6$ lymphocytes). However, lymphoblastoid clones generally secreted lower levels of antibody (less than 10 µg/ml) and, as was observed with the hybridomas, displayed poor long-term stability (approximately 5% of the initial clones of interest were stable through three rounds of expansion). To address these limitations, tumor-reactive lymphoblastoid clones were fused with K6H6/B5 cells as described above, prior to multiple rounds of expansion.

Formation of hybridomas from lymphoblastoid cells improved the stability such that 40% of the initial lymphoblastoid clones were stable through three rounds of expansion following fusion. The combination of EBV transformation followed by fusion with a heteromyeloma cell line resulted in a higher frequency of immortalization of relevant lymphocytes than was achieved utilizing either approach alone. In addition, these clones generally secreted greater than 20 μg/ml of antibody. Hybridoma clones LH11238 and LH13 were produced by this two-step immortalization method.

The immunization and immortalization conditions used to produce hybridoma cell lines H1140, H2420, H935 LH11238 and LH13 are summarized in Table 2.

TABLE 2

Immunization and immortalization conditions used to generate hybridoma cell lines producing tumor-specific human monoclonal antibodies.

| Hybridoma | Immunization | Immortalization |
|---|---|---|
| H1140 | 5 mg H3396 plasma membrane fraction 1 | Fusion with K6H6/B5 cells |
| H2420 | 5 mg H3396 plasma membrane fraction 1 | Fusion with K6H6/B5 cells |
| H935 | confluent monolayer of mitomycin C-treated H3396 cells | Fusion with K6H6/B5 cells |
| LH11238 | 10 mg H3396 plasma membrane fraction 2 | EBV transformation and fusion with K6H6/B5 cells |
| LH13 | monolayer of $4 \times 10^4$ paraformaldehyde-fixed H3922 cells | EBV transformation and fusion with K6H6/B5 cells |

Culture supernatants from immortalized lymphocytes were initially screened for reactivity against monolayers of live primary tumor cells using an ELISA assay. This ensured that reactive antibodies recognized surface antigens, and also avoided artifacts associated with screening fixed cells. Tumor cells were plated in 96-well cell culture dishes at a cell density sufficient to produce 90–95% confluent monolayers 12–24 h later. Just prior to use the media was removed and 50 μl of supernatant from either hybridomas or EBV transformed cells was added to the wells and incubated at 4° C. for 2 h. Control wells (background) were incubated with 50 μl of fresh hybridoma media.

Following incubation, supernatants were aspirated and the cells were gently rinsed three times with 200 μl of PBS. The cells were then incubated for 1–2 h with 50 μl of goat anti-human Ig (H+L) alkaline phosphatase conjugate which had been diluted 1000-fold in 1% BSA-PBS. The detection antibody was aspirated and the cells were gently rinsed four times as described above. The plates were developed for 1 h at 25° C. by the addition of 50 μl of 10 mM phenolphthalein monophosphate in 0.2 M 2-amino-2-methyl-1-propanol, 0.5 M Tris, pH 10.2 with 0.1% sodium azide. The reaction was terminated by the addition of 50 μl of 30 mM Tris, pH 10.2, with 15 mM EDTA and the absorbance at 560 nm was determined. The background value for this assay was generally A560<0.060. Clones with absorbances 4-fold or greater above background were selected for further characterization.

Antibodies that displayed reactivity with H3396 cells were also analyzed for binding to fixed HF235 normal human fibroblasts. HF235 cells were fixed 15 min at 25° C. in 2% paraformaldehyde in PBS after removing the culture medium. The cells were then washed four times with PBS prior to use. The background value for the ELISA with fixed fibroblasts was generally A560<0.080. Minimal reactivity with the fibroblasts was defined as binding less than 2-fold above background.

In order to determine the isotype of the antibodies produced by the hybridomas, microtiter plates were coated with 0.5 μg/ml either goat anti-human IgM or goat anti-human IgG. Antibody binding was detected with goat anti-human Ig alkaline phosphate conjugate. Development of the assay was terminated when supernatant yielded a positive signal with one of the capture antibodies. Likewise, the light chain class was determined by capturing the antibody with the appropriate heavy chain reagent and detecting with goat anti-human γ or κ chain-specific alkaline phosphatase conjugate.

Immunoglobulin quantitation was performed similarly, except that supernatants containing unknown quantities of Igs were serially diluted until reactivity was undetectable. Ig concentrations were calculated from values of dilutions that fell within the linear range of the standard curve, defined by standard samples of purified polyclonal human IgM, used in the range of 0.01 to 2.0 μg/ml.

Immunoglobulins were precipitated from LH11238 hybridoma supernatant by centrifugation at 800×g for 10 min and clarification by filtration through a 0.45 μm cellulose acetate filter. The supernatant was placed in dialysis tubing ($M_r$ cut-off 12–14 kDa) and concentrated two- to four-fold by coating the tubing with Aquacide (Calbiochem) and placing it at 4° C. for 6–8 h. Excess Aquacide was removed, the dialysis bag rinsed, and the sample was dialyzed 12–24 h versus multiple changes of ice-cold distilled water. The precipitated antibody was collected by centrifugation at 10,000×g for 30 min. The supernatant was removed and the pellets were resuspended in a minimal volume of warm 10-fold concentrated PBS. Following solubilization of most of the pellet, the buffer concentration was adjusted to PBS and the insoluble material was removed by centrifugation at 10,000×g for 30 min. Antibodies H1140, H2420 and H935 could similarly be precipitated in low ionic strength buffer.

The LH13 antibody was not precipitated in low ionic strength buffer. Therefore, in order to obtain concentrated antibody the volume of the clarified supernatant was reduced with an Amicon apparatus utilizing a YM-30 membrane. The antibody was concentrated greater than 50-fold by this approach.

Five percent of the hybridomas screened (372/7216) bound tumor surface antigens greater than four-fold above background. Of these 372 clones, 55 (15%) produced antibodies that did not bind fibroblasts significantly. Although numerous antibody-secreting hybridomas were isolated from control MLRs that had not been incubated with tumor cells or membrane fractions, none of these antibodies displayed preferential tumor reactivity. Approximately 20% (11/55) of hybridomas producing antibodies that displayed tumor specificity were stable through multiple expansions in culture. Five of these clones secreted greater than 20 μg/ml antibody. The properties of these clones are summarized in Table 2. All five antibodies were of the IgM isotype and displayed a range of immunoreactivities as determined by assaying on fixed monolayers of H3396 cells. At least one antibody was generated from each of the culture conditions and immortalization procedures employed. The two antibodies displaying the greatest immunoreactivity, LH13 and LH11238, were characterized further (below).

The properties of the tumor-specific human monoclonal antibodies produced by hybridoma cell lines H1140, H2420, H935 LH11238 and LH13 are summarized in Table 3.

TABLE 3

Characteristics of tumor-specific human monoclonal antibodies.

| Hybridoma | Isotype/ Light chain class | Secretion Level (μg/ml)[a] | Immuno-Reactivity[b] | Precip-itation[c] |
|---|---|---|---|---|
| H1140 | IgM/λ | 40 | 1.0 | + |
| H2420 | IgM/λ | 63 | 1.3 | + |
| H935 | IgM/λ | 36 | 1.4 | + |
| LH11238 | IgM/κ | 29 | 5.7 | + |
| LH13 | IgM/λ | 26 | 341 | − |

[a]Secretion level is typical value obtained from supernatant of a terminal culture
[b]Immunoreactivity (ΔA560/[(μg Ig)(min)]) determined on confluent paraformaldehyde-fixed H3396 monolayers and normalized to immunoreactivity of H1140
[c]Precipitation denotes ability (+) or inability (−) to precipitate antibody in low ionic strength buffer In summary, this example shows that an unstimulated human immune repetoire (splenocytes from non-tumor-bearing patients) can be used to generate human monoclonal antibodies reactive with novel tumor antigens. This was achieved through the stimulation of MLR cultures with either whole tumor cells or membrane fractions derived from tumor cells. The specificity of the antigen stimulation was demonstrated by the generation of tumor-specific antibodies as well as by the absence of tumor-specific antibodies from cultures not treated with tumor cells or membrane fractions.

EXAMPLE II

Immunoreactivities of LH13 and LH11238 Antibodies

This Example shows the immunoreactivities of LH13 and LH11238 antibodies with a panel of human tumor cells.

In order to use LH13 and LH11238 antibodies for immunodiagnostic and immunotherapeutic purposes, the range of tumor types expressing the corresponding antigens needs to be identified. Tumor cell lines are representative of the corresponding tumor type, and normal fibroblasts are representative of non-neoplastic tissues. The tumor cell lines were derived from melanomas, lung carcinomas, ovarian carcinomas and breast carcinomas. The human monoclonal antibodies of the invention were tested for immunoreactivity with both human cancer cell lines and normal fibroblasts.

H3396, H3464, H3477 and H3922 are cultured cell lines established from metastases of human breast adenocarcinoma, which were explanted and maintained in culture. H2981 and H2987 are cultured cell lines established from human lung carcinomas, which were explanted and maintained in culture. H3639 and H3723 are culture cell lines established from human ovarian carcinomas, which were explanted and maintained in culture. Each cell line was derived from a different explant.

Immunoreactivities were determined by the ELISA procedure described above, by incubating a broad range of antibody concentrations with fixed monolayers of tumor cells. Antibody binding was measured with saturating quantities of detect antibody. Antibody binding was measured as the ΔA560/[(μg Ig) (min)] in the linear range of the assay. The immunoreactivities of tumor-specific human monoclonal antibodies against a panel of tumor and normal cells are presented in Table 4.

TABLE 4

Immunoreactivity of human monoclonal antibodies LH13 and LH11228 against tumor and normal cells.

| | | Immunoreactivity (ΔA560/[(μg Ig) (min)]) | |
|---|---|---|---|
| Cell Line | Description | LH13 | LH11238 |
| HF285 | normal fibroblast | 0 | 0 |
| H2669 | melanoma | 0 | 0 |
| H3774 | melanoma | 0 | 0 |
| H3396 | breast carcinoma | 1.136 | 0.019 |
| H3464 | breast carcinoma | 0.507 | 0.022 |
| H3477 | breast carcinoma | 0.046 | 0.008 |
| H3922 | breast carcinoma | 0[a] | 0 |
| H2981 | lung carcinoma | 0.584 | 0 |
| H2987 | lung carcinoma | 0 | 0 |
| H3639 | ovarian carcinoma | 0[a] | 0.011 |
| H3723 | ovarian carcinoma | 2.602 | 0.026 |

[a]Exhibited substantial immunoreactivity upon permeabilization of cells with 0.1% digitonin As shown in Table 4, LH13 displayed a broad cross-reactivity on the panel of tumor cells with high (H3723 and H3396), intermediate (H2981 and H3464), and low (H3477) immunoreactivities. The LH13 antigen was absent or present at undetectable levels on intact normal fibroblasts (HF285), melanomas (H2669 and H3774), and with several of the intact carcinomas tested (H3922, H2987, and H3639). The lack of reactivity with H3922 cells was particularly surprising because the LH13 antibody was isolated from lymphocytes which had been stimulated with H3922 cells. To examine this more closely each of the cell lines was permeabilized with 0.1% digitonin and their reactivity with LH13 was re-examined. Two of the cell lines which were completely negative when intact cells were assayed, H3922 and H3639, bound the LH13 antibody under conditions in which the antibody had access to intracellular compartments. Furthermore, H2981 cells, which had an intermediate LH13 immunoreactivity when assayed under non-permeabilizing conditions were highly reactive under permeabilizing conditions (immunoreactivity greater than 7.0). The data obtained for immunoreactivities in the presence and absence of 0.1% digitonin could not be compared directly, however, due to differential cell loss from the cell culture dishes during the incubations.

LH11238 displayed a similar reactivity profile, though the magnitude of its immunoreactivity was always much less than that of the LH13 antibody. Reactivity was observed with intact H3396, H3464, H3477, H3639, and H3723. Other cells tested were negative, including the fibroblast and melanoma cell lines. Based on the immunoreactivity determinations made for each of the cell lines with LH13 and LH11238 it appears unlikely that these antibodies recognize the same epitope. For instance, LH13 displayed moderate immunoreactivity with the H2981 lung carcinoma line while no binding of LH11238 to this cell line was detected. Likewise, LH11238 bound intact H3639 ovarian carcinoma cells, even though binding of LH13 could not be detected under identical incubation conditions.

EXAMPLE III

Binding Activity of LH13 and LH11238 Human Monoclonal Antibodies

This Example shows the binding activity of human monoclonal antibodies LH13 and LH11238 with normal and tumor cells.

In order to determine the immunoreactivity of human monoclonal antibodies with live tumor cells and normal cells, flow cytometry (FACS analysis) was used. H3464 breast tumor cells were chosen because they expressed both LH13 and LH11238 antigens by ELISA analysis and were readily isolated as a single cell suspension. Normal peripheral blood lymphocytes were also examined as representative of normal tissues. Facs analysis additionally permits examination of heterogeneity of a cell population with respect to antigen expression.

H3464 cells were removed from culture dishes with trypsin or Versene (EDTA), washed with PBS, resuspended at $2 \times 10^6$ cells/ml in tumor media, and allowed to recover 2 h at 37° C. Antibodies were incubated at 5.0 μg/ml with $1 \times 10^6$ tumor cells in 50 μl total volume for 30 min on ice. The cells were washed once with 1.0 ml of ice-cold PBS, incubated with 2 μg/ml FITC-labeled goat anti-human IgM diluted in 1% BSA-PBS for 30 min on ice, and washed once more with 1.0 ml of ice-cold PBS. Antibody binding to cells was analyzed with a Becton Dickinson FACSort.

Consistent with the ELISA results, H3464 cells incubated with LH11238 and FITC-labeled antihuman IgM displayed a shifted staining pattern relative to an irrelevant control human IgM (FIG. 1A). Greater than 90% of the cells tested bound LH11238 antibody, though the broad range of fluorescent intensities observed was consistent with heterogeneous expression levels of the antigen on these tumor cells. Similar FACS staining profiles were also observed with H935, H2420, and H1140.

Surprisingly, LH13 antibody, which was 23-fold more reactive than LH11238 on H3464 cells as determined by ELISA (Table 4) displayed little shift (FIG. 1B). To determine if the LH13 antigen was particularly sensitive to the proteolytic conditions used to isolate the tumor cells for analysis (trypsin), cells were allowed longer recovery periods following isolation or non-proteolytic cell isolation methods were utilized, such as Versene (EDTA) release. Neither of these approaches resulted in significantly greater staining of the tumor cells.

Facs analysis of normal human cells, such as peripheral blood lymphocytes, was negative for each of the antibodies tested, consistent with the ELISA results obtained with normal fibroblast cells.

EXAMPLE IV

Characterization of LH11238 Antigen

This Example describes the subcellular characterization of the LH11238 antigen.

Both the ELISA screening and the FACS analysis of live cells described above demonstrated the expression of LH11238 antigen on the plasma membrane of tumor cells. However, these approaches did not examine the distribution of the antigen on intracellular structures of carcinoma-derived cells. To examine the intracellular localization of LH11238 antigen, immunofluorescence analysis was used.

Monolayers of H3464 cells were seeded on 12-mm round coverslips (No. 1 thickness, 0.06–0.13 mm thick) one day prior to use and were fixed with 2% paraformaldehyde in PBS for 15 min at 25° C. The cells were rinsed twice with PBS and incubated with 50 μl/ml antibody diluted either in 1% BSA-PBS (non-permeabilized) or in 1% BSA-PBS containing 0.1% digitonin (permeabilized) for 2 h at 4° C. The cells were rinsed twice with PBS and were then incubated in the dark with FITC-labeled goat anti-human IgM diluted 1:500 in the same buffer as the primary antibody. The cells were rinsed 4 times with PBS and the coverslips were mounted in Fluoromount-G (Southern Biotechnology). Cells were visualized with an Olympus microscope equipped with epifluorescent optics and an Olympus Splan 40× (NA 0.70) objective lens.

Non-permeabilized, paraformaldehye-fixed H3464 cells stained with the LH11238 antibody displayed surface staining consistent with localization to the plasma membrane. Consistent with the FACS analysis, greater than 70% of fixed H3464 cells bound LH11238. When H3464 cells were permeabilized to allow access to intracellular structures, punctate, peri-nuclear staining was observed. LH11238 binding to H3464 cells was specific as control incubations with irrelevant, isotype and concentration-matched human antibodies did not stain intact or 0.1% digitonin permeabilized cells. The punctate, peri-nuclear staining observed on permeabilized cells suggested localization of the antigen in the lysosomes. To verify this, cells were stained with antibodies to CD63, a known lysosomal glycoprotein. Incubation of H3464 cells with antibody to CD63 stained intracellular structures similar to those labeled with LH11238, consistent with a lysosomal localization of intracellular LH11238.

Based on these results it was concluded that the LH11238 antigen is present both on the plasma membrane and in the lysosomes of H3464 cells.

EXAMPLE V

Internalization of LH11238 Antigen

This Example shows that LH11238 antigen is internalized from the plasma membrane to lysosomal compartments.

Immunofluorescence experiments described above indicated that LH11238 antigen was present on both the cell surface and in lysosomes of tumor cells. The dual localization could result from LH11238 antigen being co-expressed in lysosomes and the cell surface, or from being internalized to endosomal/lysosomal compartments. In order to determine whether LH11238 antigen was internalized, the procedure for immunofluorescent localization was modified.

Monolayers of live H3464 cells were chilled on ice for 30–60 min to completely inhibit endocytosis. The cells were then washed, incubated with LH11238 antibody, washed again, and incubated with FITC-labeled goat anti-human IgM antibody. The cells were maintained at 4° C. throughout all of the preceeding steps to ensure complete inhibition of endocytosis. The cells were then shifted to 37° C. with pre-warmed cell culture media. At various intervals the cells were shifted back to 4° C. and fixed with 2% paraformaldehyde. Initially, diffuse surface staining was observed, identical to that observed with non-permeabilized fixed cells. Following 10 min at 37° C., clustering of the LH11238 antibody at multiple sites on the cell surface was observed. With longer incubation times, LH11238 first localized to a few sites on the cell surface, and then began to internalize. These staining patterns were not observed if cells were incubated with irrelevant primary antibodies, incubated with secondary antibody only, or if the cells were maintained at 4° C. for the duration of the experiment. These results are consistent with LH11238 binding and being internalized by H3464 cells.

In summary, the LH11238 antibody was first characterized as a surface antigen based on ELISA analysis of intact cells, FACS analysis of live cells, and immunolocalization using non-permeabilized cells. However, further immunolocalization studies with permeabilized cells demonstrated that a portion of this antigen was also localized to a punctate, peri-nuclear compartment. Similar staining was observed with cells incubated with anti-CD63 antibody, a lysosomal protein. Consistent with the dual localization of the LH 11238 antigen on plasma membranes and in the lysosomes, it was demonstrated that antibody bound to the surface of live cells was internalized. The dual localization of tumor antigens to the plasma membrane and lysosomes has been observed previously. For instance, the BR96 antibody binds the lysosomal-associated membrane protein lamp-1 on the surface of intact tumor cells, even though lamp-1 is normally an integral membrane protein predominantly located in the lysosomal compartment. In addition, the secretion of elevated levels of soluble lysosomal proteins, such as cathespins B, D, and L from tumor cells has also been documented. A portion of the secreted cathespin D is bound by the mannose 6-phosphate receptor and internalized. At present, it is unclear whether LH11238 is soluble or an integral membrane protein. However, the antigen is found in the soluble fraction of a TX-114 phase separation of cell extracts, consistent with LH11238 being membrane-associated as opposed to an integral membrane protein.

EXAMPLE VI

Characterization of LH13 Antigen

This example shows the localization of the LH13 antigen.

The LH13 antibody exhibited significant immunoreactivity when assayed by ELISA on fixed monolayers of carcinoma-derived cell lines, as described above. However, FACS analysis suggested that LH13 bound only poorly to cell surfaces. Further ELISA analysis indicated that LH13 antigen was predominantly present in a compartment that was only accessible to antibody when the cells were treated with 0.1% digitonin. To further examine the expression of LH13 antigen in either subcellular compartments or in the secreted medium, immunofluorescence analysis and direct ELISA analysis were used.

To examine the subcellular localization of LH13 antigen, immunofluorescence was performed on paraformaldehyde-fixed H3464 cells as described above. Incubation of LH13 antibody with unpermeabilized H3464 cells (as described above using LH11238 antibody) resulted in weak staining of the cell surface, consistent with the slight shift observed by FACS analysis. Incubation of LH13 antibody with permeabilized H3464 cells by immunofluorescence resulted in no detectable staining. Possibly, little LH13 is associated with intracellular structures in H3464 cells or intracellular forms of LH13 were not recognized by the antibody in this cell line.

These results could also indicate that LH13 antigen was predominantly secreted. To observe secreted LH13 antigen, a constant amount of LH13 antibody (0.01 µg/ml)was diluted into increasing amounts of culture media which had been removed from confluent monolayers of H3396 cells (conditioned media). Conditioned media was then assayed for binding to fixed H3396 monolayers. A modest reduction (approximately 15%) in the binding of the LH13 antibody to the monolayer was observed with increasing concentrations of conditioned media (FIG. 2A), consistent with LH13 antigen being present in the media. No reduction in the binding of the LH13 antibody to the monolayer was observed with increasing concentrations of conditioned media from H3922 cells.

Figure 2:
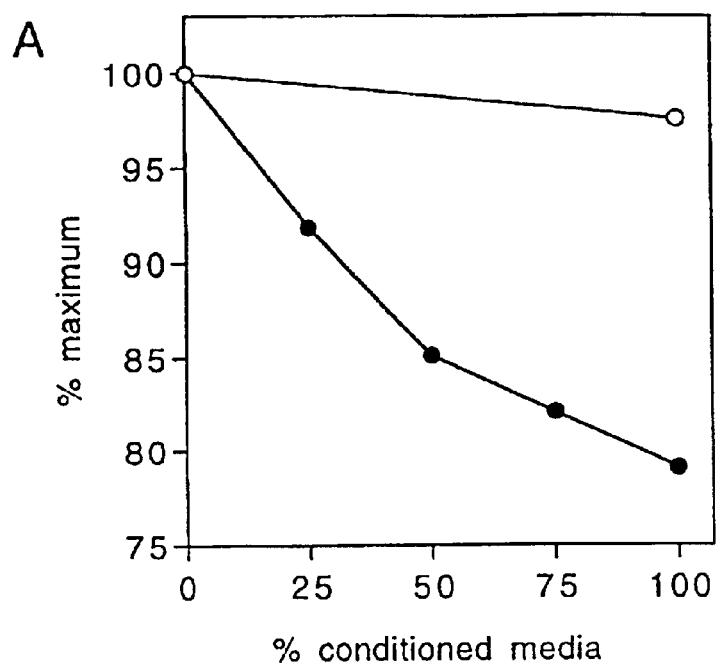
FIG. 2 shows that LH13 antigen is secreted by H3396 cells.
Figure 2:
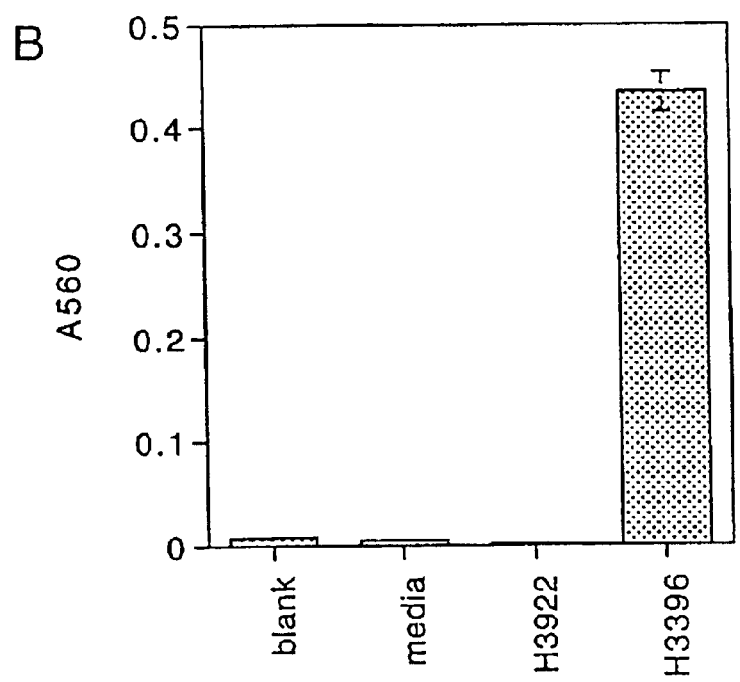

To observe LH13 antigen in conditioned media of H3396 cells, a direct ELISA format was used. Conditioned media was incubated in a 96-well cell culture dish for 10–12 h at 4° C., removed, and the washed wells were subsequently assayed for LH13 antibody binding. The antigen present in conditioned media obtained from H3396 cells bound to the culture dish and was readily detected (FIG. 2B). The specificity of antibody binding was demonstrated by incubating LH13 antibody with cell culture wells that had been pre-treated with: (1) conditioned media from a tumor line expressing undetectable quantities of LH13 (H3922), (2) fresh media (media), or (3) nothing (blank). None of these pre-incubation conditions resulted in detectable LH13 binding to the well (FIG. 2B).

In summary, characterization of the LH13 antigen demonstrated that the majority of this antigen is found in conditioned media. Based on this observation, it was concluded that LH13 is secreted from tumor cells.

EXAMPLE VI

Purification and Further Characterization of LH13 Antigen

This example describes the purification and further characterization of LH13 antigen.

As described above, the LH13 antigen is secreted from breast tumor cells and displays a surprisingly high affinity for cell culture dishes. These observations suggested that LH13 antigen could be readily purified from conditioned H3396 media using its binding to culture dishes as a means of monitoring its purification. Once the LH13 antigen is purified, its susceptibility to various reagents could readily be determined to further characterize its properties.

As a first step in enriching the LH13 antigen, the H3396 cell line was adapted to grow in serum-free media supplemented with minimal protein [Iscove's media supplemented with TCH (Celox, defined serum replacement), 2 mM L-glutamine, non-essential amino acids, and 1 mM sodium pyruvate]. Cells grown under these conditions secreted comparable levels of the antigen as grown in the presence of serum. Conditioned media was collected, pooled, and 250 ml was diluted to 1 liter with water to reduce the ionic strength. The diluted media was applied at 3 ml/min to a 11 cm×1.5 cm column of Q SEPHAROSE FAST FLOW agarose resin which had been equilibrated with 0.25-fold concentrated (0.25×) PBS. The majority of the antigen bound to the column as demonstrated by the lack of reactivity of the flow-through fraction. After washing the column with 200 ml of 0.25×PBS, protein was eluted at a flow rate of 6 ml/min with a 90 min linear gradient from 100% 0.25×PBS to 70% 0.5 M NaCl in 0.25×PBS.

Column fractions were assayed for protein content with the BCA protein assay using BSA as the standard. Column fractions were assayed for LH13 antigen as follows. Each fraction was diluted 10-fold into water and 50 µl/well was transferred to a sterile 96-well cell culture dish for 12 h at 4° C. The plate was washed twice with PBS and incubated with 10 µg/ml LH13 antibody diluted in 1% BSA-PBS for 2 h at 37° C. The plate was then washed four times with PBS, incubated with goat anti-human Ig alkaline phosphatase conjugate diluted 1000-fold into 1% BSA-PBS for 1 h at 25° C., and was developed as described above.

Figure 3:
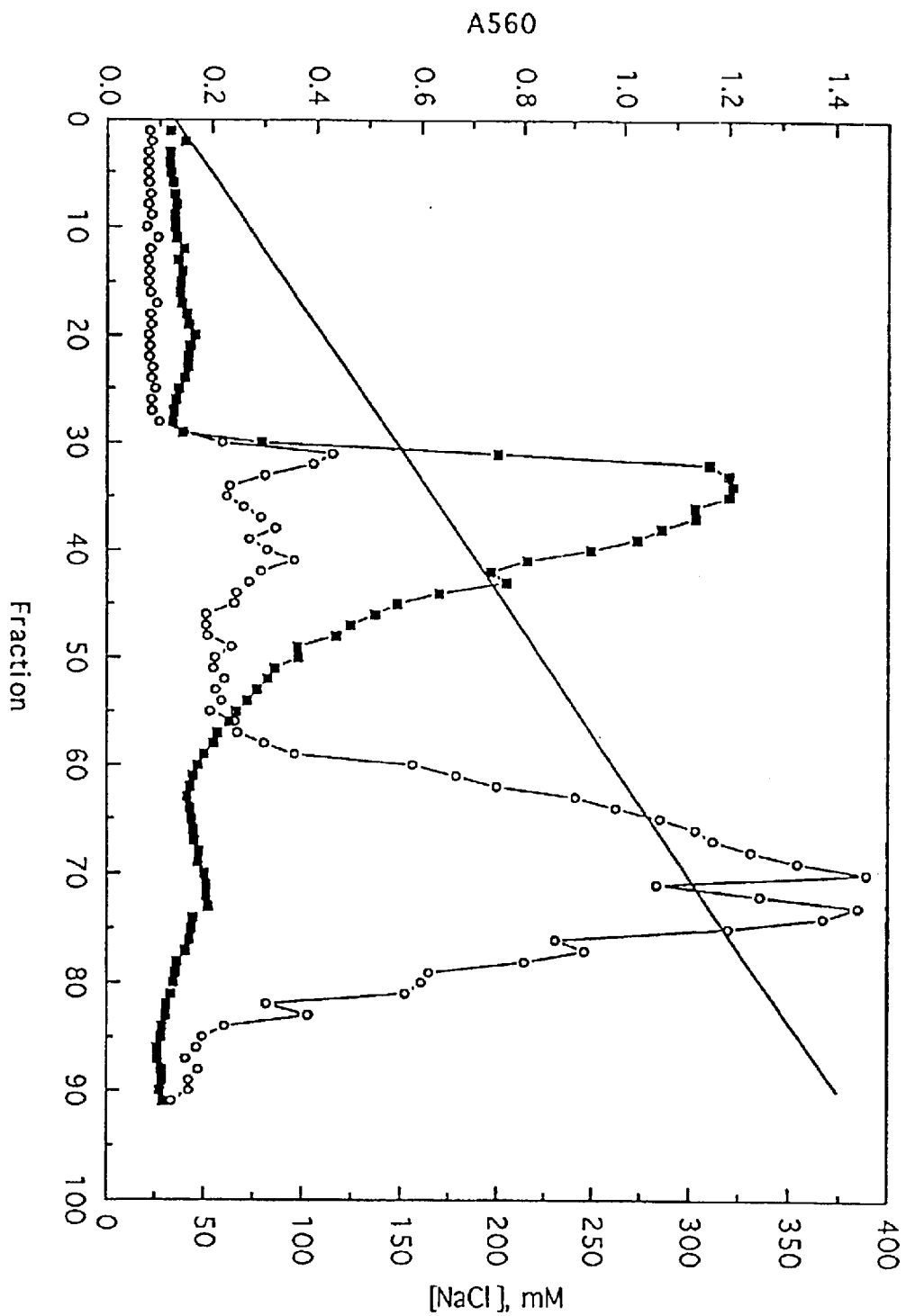
FIG. 3 shows the purification of LH13 antigen by anion exchange chromatography on a Q Sepharose column.

Most of the protein eluted between 150 mM and 250 mM NaCl (FIG. 3, closed circles), while the majority of the LH13 antigen eluted above 250 mM NaCl (FIG. 3, open circles). The specific activity (ELISA signal/[protein]) of the peak antigen fraction was 200-fold greater than the starting material. As a control, LH13 antigen was diluted with a range of NaCl concentrations (50 mM to 400 mM) to determine if the ionic strength affected binding to the cell culture dishes. The range of NaCl concentrations employed for binding and eluting LH13 from the column did not affect antigen binding to the cell culture dish. Therefore, the direct ELISA accurately reflects the distribution of antigen in the various column fractions.

Column fractions were further resolved by electrophoresis on 4–20% SDS-polyacrylamide gradient gels. Coomassie blue staining revealed a single major protein in the most reactive fractions, but Western blots of the various column fractions failed to identify this as the LH13-reactive antigen.

Figure 4:
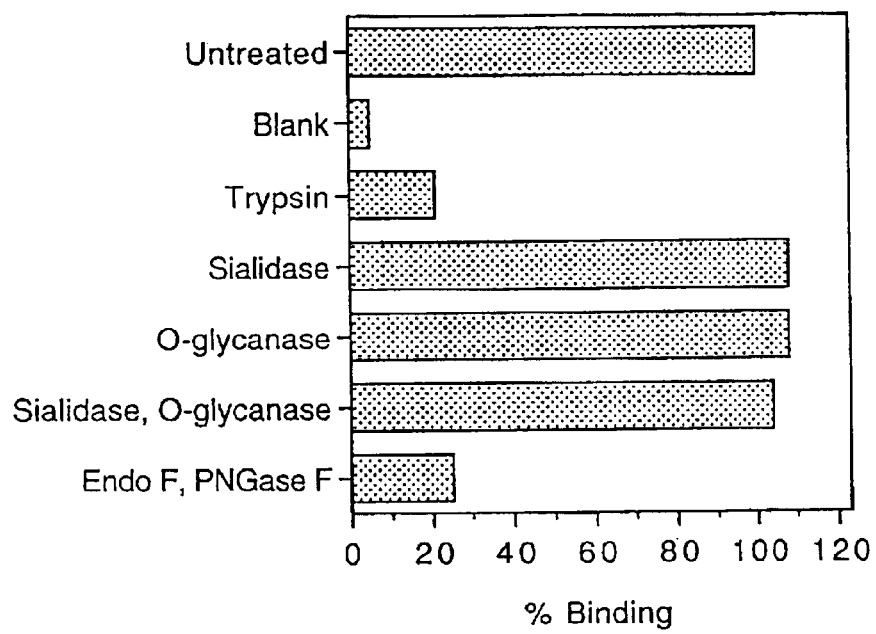
FIG. 4 shows that LH13 antigen is susceptible to trypsin and endoglycosidase-F/peptide-N-lycosidase F treatment.

To further characterize the LH13 antigen, its susceptibility to a variety of treatments was examined using the direct ELISA method. LH13 antigen was coated on cell culture dishes, as described above, and incubated under a variety conditions. LH13 antigen was incubated with 5 mg/ml trypsin at 37° C. for 30 min. Alternatively, LH13 antigen was denatured by treatment with 10% SDS+2% β-mercaptoethanol at 37° C. for 30 min. prior to treatment with 2 U/ml sialidase (Oxford GlycoSystems), 400 U/ml endoglycosidase-F/peptide-N-glycosidase F (Endo F, PNGase F) (Oxford GlycoSystems), 60 mU/ml endo-α-N-acetylgalactosaminidase (O-glycanase) (Oxford GlycoSystems), or 2 U/ml sialidase plus 60 mU/ml endo-α-N-acetylgalactosaminidase (Sialidase, O-glycanase) at 37° C. for 24 h. The culture dishes were washed three times with PBS and assessed for LH13 antibody binding as described above. The effect of each treatment was compared to control samples which were treated under identical conditions with buffer alone (FIG. 4).

Treatment of LH13 antigen with 10% SDS±2% β-mercaptoethanol, sialidase, or endo-α-N-acetylgalactosaminidase (O-glycanase) had little effect on subsequent binding of antibody. The resistance of the antigen to treatment with sialidase and O-glycanase was not affected by denaturing the antigen prior to treatment nor by simultaneous treatment with both glycosidases. Binding of antibody in the direct ELISA was reduced by treatment with trypsin (79%, FIG. 4) or with endoglycosidase-F/peptide-N-glycosidase F (36%, not shown). The binding of antibody to LH13 denatured with 10% SDS+2% β-mercaptoethanol prior to treatment with endoglycosidase-F/peptide-N-glycosidase F was further diminished, reducing binding by 75% as compared to untreated samples (FIG. 4).

Due to the broad range of specificities of endoglycosidase-F/peptide-N-glycosidase F it was not possible to reach specific conclusions regarding the structure of the carbohydrate. However, binding of LH13 antibody was completely unaffected by treatment with sialidase, which removes N- or O-acyl, non-reducing terminal sialic acids. Treatment with endo-α-N-acetylgalactosaminidase, which removes Galβ1-3GalNAc associated with serine or threonine, or the combination of sialidase and endo-α-N-acetylgalactosaminidase also did not affect antibody binding. Trypsin sensitivity of antibody binding to antigen suggested that the epitope is associated with a protein component.

In summary, LH13 antigen was purified more than 200-fold from H3396 serum-free conditioned medium, using anion exchange chromatography. Preliminary studies indicated that purified LH13 antigen is excluded from a Superdex 75 gel filtration column, consistent with the antigen being larger than 70 kDa. Treatment of LH13 antigen bound to cell culture plates with a variety of reagents provided evidence that both carbohydrate and protein components are present, and are involved in either binding of the epitope to LH13 antibody or binding LH13 antigen to tissue culture plates. At present, it is not possible to distinguish between these two possibilities.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A human monoclonal antibody or functional fragment thereof, comprising the amino acid sequence of SEQ ID NO:2, or having a conservative substitution of an amino acid thereof, and the amino acid sequence of SEQ ID NO:4, or having a conservative substitution of an amino acid thereof, wherein said antibody or functional fragment thereof binds a neoplastic cell or antigen thereof and wherein said antibody or functional fragment thereof having a conservative substitution of an amino acid binds the same neoplastic cell or antigen thereof as said antibody or functional fragment comprising SEQ ID NOS:2 and 4.

2. The human monoclonal antibody of claim 1, wherein said functional fragment is selected from the group consisting of Fv, Fab, Fab', or F(ab')$_2$.

3. The human monoclonal antibody or functional fragment of claim 1, further comprising a label.

4. The human monoclonal antibody or functional fragment of claim 3, wherein said label comprises a cytotoxic or cytostatic agent.

5. A human monoclonal antibody of functional fragment thereof, comprising a heavy chain variable region having the three CDR sequences of the amino acid sequence of SEQ ID NO:2, or having a conservative substitution of an amino acid thereof, and a light chain variable region having the three CDR sequences of the amino acid sequence of SEQ ID NO:4, or having a conservative substitution of an amino acid thereof, wherein said antibody or functional fragment thereof binds a neoplastic cell or antigen thereof and wherein said antibody or functional fragment thereof having a conservative substitution of an amino acid binds the same neoplastic cell or antigen thereof as said antibody or functional fragment comprising SEQ ID NOS:2 and 4.

6. The human monoclonal antibody or functional fragment of claim 1, further comprising a physiologically acceptable compound.

7. The human monoclonal antibody of claim 1, wherein said human monoclonal antibody is purified.

* * * * *